(12) United States Patent
Chang et al.

(10) Patent No.: US 10,351,630 B2
(45) Date of Patent: Jul. 16, 2019

(54) ASSAY TO DETECT HUMAN DPP-4

(71) Applicant: MEDIMMUNE, LLC, Gaithersburg, MD (US)

(72) Inventors: Chien-Ying Chang, Gaithersburg, MD (US); Xiaodong Xiao, Gaithersburg, MD (US); Partha Chowdhury, Gaithersburg, MD (US)

(73) Assignee: MEDIMMUNE, LLC, Gaithersburg, MD (US)

( * ) Notice: Subject to any disclaimer, the term of this patent is extended or adjusted under 35 U.S.C. 154(b) by 519 days.

(21) Appl. No.: 14/991,160

(22) Filed: Jan. 8, 2016

(65) Prior Publication Data

US 2016/0200832 A1 Jul. 14, 2016

Related U.S. Application Data

(60) Provisional application No. 62/101,697, filed on Jan. 9, 2015.

(51) Int. Cl.
*C07K 16/28* (2006.01)
*C07K 16/40* (2006.01)
*G01N 33/573* (2006.01)
*C12Q 1/37* (2006.01)

(52) U.S. Cl.
CPC .......... *C07K 16/40* (2013.01); *C07K 16/2896* (2013.01); *C12Q 1/37* (2013.01); *G01N 33/573* (2013.01); *C07K 2317/565* (2013.01); *C07K 2317/76* (2013.01); *G01N 2333/948* (2013.01)

(58) Field of Classification Search
None
See application file for complete search history.

(56) References Cited

U.S. PATENT DOCUMENTS

| | | | |
|---|---|---|---|
| 5,892,019 A | 4/1999 | Schlom et al. | |
| 6,413,746 B1 | 7/2002 | Field | |
| 6,660,501 B2 | 12/2003 | Field | |
| 7,462,698 B2 * | 12/2008 | Aoyagi | C07K 16/2896 530/387.3 |
| 7,829,090 B2 | 11/2010 | Monk et al. | |
| 2003/0023991 A1 * | 1/2003 | Zonana | C07K 14/47 800/8 |
| 2008/0187954 A1 | 4/2008 | Kallmeier et al. | |
| 2009/0155784 A1 | 6/2009 | O'Toole et al. | |
| 2010/0221752 A2 | 9/2010 | Gold et al. | |
| 2012/0052060 A1 | 3/2012 | Monk et al. | |
| 2013/0281876 A1 | 10/2013 | Faggioni et al. | |
| 2013/0310266 A1 * | 11/2013 | Liang | G01N 33/564 506/9 |

FOREIGN PATENT DOCUMENTS

| | | |
|---|---|---|
| WO | WO 2004/009823 | 1/2004 |
| WO | WO 2004/104216 | 12/2004 |
| WO | WO 2009/124090 | 10/2009 |
| WO | WO 2012/083132 | 6/2012 |
| WO | WO 2012/158954 | 11/2012 |
| WO | WO 2015/112970 | 7/2015 |

OTHER PUBLICATIONS

Hemken et al. "Development and analytical performance of a new ARCHITECT automated dipeptidyl peptidase-4 immunoassay", Practical Laboratory Medicine vol. 9, Dec. 2017, pp. 58-68, Dec. 2017, doi: 10.1016/j.plabm.2017.10.003 (Year: 2017).*
Harlow et al. "Antibodies: A Laboratory Manual" (1988) Cold Spring Harbor Laboratory Press, Cold Spring Harbor, NY, 1988, pp. 25-26 and 37-59 (Year: 1988).*
Edwards et al. "The remarkable flexibility of the human antibody repertoire; isolation of over one thousand different antibodies to a single protein, BLyS" J. Mol. Biol. (2003) 334, 103-118, DOI: 10.1016/j.jmb.2003.09.054 (Year: 2003).*
Lloyd et al. "Modelling the human immune response: performance of a 10e11 human antibody repertoire against a broad panel of therapeutically relevant antigens", Protein Engineering, Design and Selection, vol. 22, Issue 3, Mar. 1, 2009, pp. 159-168, https://doi.org/10.1093/protein/gzn058 (Year: 2009).*
Meyer et al. "New Insights in Type I and II CD20 Antibody Mechanisms-Of-Action With a Panel of Novel CD20 Antibodies", British Journal of Haematology, 2018, 180, 808-820, |https://doi.org/10.1111/bjh.15132 (Year: 2018).*
Brown et al. "Tolerance of single, but not multiple, amino acid replacements in antibody VH CDR 2: a means of minimizing B cell wastage from somatic hypermutation?", J Immunol. May 1996;156(9):3285-91 (Year: 1996).*
Vajdos et al. "Comprehensive functional maps of the antigen-binding site of an anti-ErbB2 antibody obtained with shotgun scanning mutagenesis" J Mol Biol. Jul. 5, 2002;320(2):415-28, DOI: 10.1016/S0022-2836(02)00264-4 (Year: 2002).*
Lederman et al. "A single amino acid substitution in a common african allele of the CD4 molecule ablates binding of the monoclonal antibody, OKT4", Molecular Immunology 28: 1171-1181, 1991, doi:0161-5890(91)90003-3 (Year: 1991).*
Colman et al. Research in Immunology, 1994; 145(1): 33-36 (Year: 1994).*
U.S. Appl. No. 61/931,878, U.S. Appl. No. 61/990,932, 2016/0363591, filed Dec. 15, 2016, Streicher et al.
U.S. Appl. No. 61/936,967, 2016/0200832, filed Jul. 14, 2016, Chang et al.
Abbott et al., "Genomic organization, exact localization, and tissue expression of the human CD26 (dipeptidyl peptidase IV) gene," Immunogenetics, 1994, 40(5):331-8.

(Continued)

*Primary Examiner* — Christine Foster
(74) *Attorney, Agent, or Firm* — Casimir Jones, S.C.; Melissa E. Kolom

(57) ABSTRACT

This disclosure provides a robust, sensitive, and specific assay for the detection and measurement of DPP-4 levels in samples obtained from human patients. The disclosure further provides novel anti-DPP-4 monoclonal antibodies that recognize human DPP-4, and assay kits comprising one or more of these antibodies.

15 Claims, 9 Drawing Sheets

Figure 1:
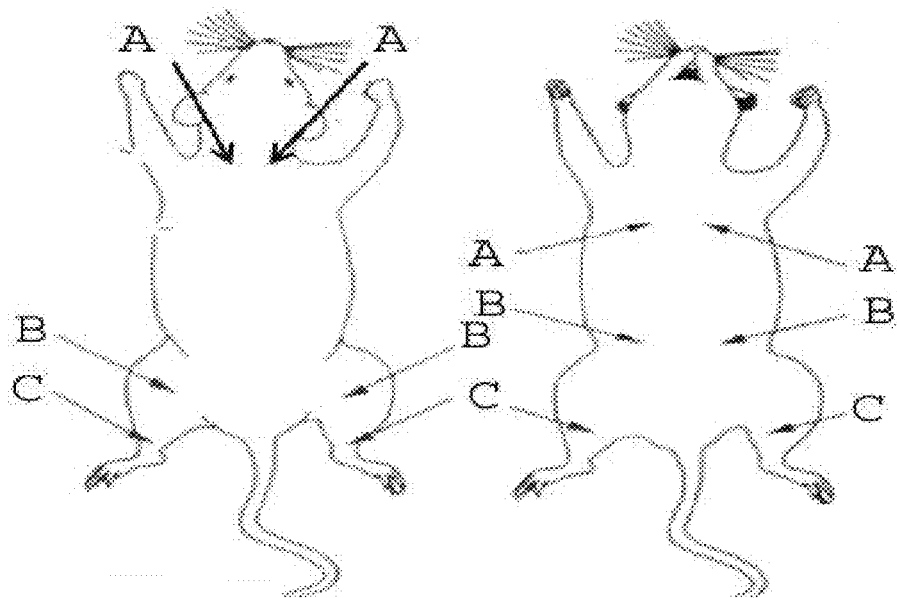

Specification includes a Sequence Listing.

(56) References Cited

OTHER PUBLICATIONS

American Thoracic Society, "Idiopathic pulmonary fibrosis: diagnosis and treatment. International consensus statement," Am. J. Respir. Crit. Care Med., 2000, 161:646-664.
Antoniu SA., "Pitrakina, a dual IL-4/IL-13 antagonist for the potential treatment of asthma and eczema," Curr Opin Investig Drugs, 2010, 11:1286-94.
Aytac et al., "CD26/dipeptidyl peptidase IV: a regulator of immune function and a potential molecular target for therapy," Curr Drug Targets Immune Endocr Metabol Disord, 2004, 4(1):11-8.
Bender, BG., "Overcoming barriers to nonadherence in asthma treatment," J. Allergy Clin. Immunol, 2002, 109:S554-9.
Bieber, "Atopic Dermatitis," New England Journal of Medicine, 2008, 358: 1483-1494.
Blanchard & Rothenberg, "Chemotactic factors associated with eosinophilic gastrointestinal diseases," Immunol. Allergy Clin. North. Am., 2009 29:141-148.
Blanchard et al., "Periostin facilitates eosinophil tissue infiltration in allergic lung and esophageal responses," Mucosal Immunol., 2008, 1 :289-296.
Brightling et al., "Efficacy and Safety of Tralokinumab, an Anti-IL-13 Monoclonal Antibody, in A Phase 2b Study of Uncontrolled Severe Asthma," Am J Respir Crit Care Med, 2014, I89:A6670.
British Thoracic Society, "British guideline on the management of asthma," Thorax, 2003, 58 Suppl 1:i1-94.
Chen et al., "Interleukin-13—1112 C/T Promoter Polymorphism Confers Risk for COPD: A Meta-Analysis," PLoS One, 2013 8:e68222.
Chothia et al., "Canonical structures for the hypervariable regions of immunoglobulins," J. Mol. Biol., 1987, 196:901-917.
Choy et al, "Gene expression patterns of Th2 inflammation and intercellular communication in asthmatic airways," J. Immunol., 2011, 186(3):1861-1869.
Conarello et al., "Mice lacking dipeptidyl peptidase IV are protected against obesity and insulin resistance," Proc Natl Acad Sci USA, 2003, 100(11):6825-30.
Danese et al., "Ulcerative Colitis," N Engl J Med., 2011 365(18):1713-25.
Dente et al., "Cytokines in Induced Sputum: A Role for the Ratio of IL-6/IL-13 in the Differentiation of Asthma and Chronic Obstructive Pulmonary Disease?" Respiration, 2012, 84:98-100.
Expert Panel Report 3: Guidelines for the Diagnosis and Management of Asthma, National Asthma Education and Prevention Program (2007) ("NAEPP Guidelines").
Fish, L. and C. L. Lung, "Adherence to asthma therapy," Ann Allergy Asthma Immunol, 2001, 86:24-30.
Gina, "Global Strategy for Asthma Management and Prevention," National Institute of Health, 2002.
Gines et al., "Regulation of epithelial and lymphocyte cell adhesion by adenosine deaminase-CD26 interaction," Biochem. J., 2002, 361 :203-209.
Giovannini-Chami et al., "Distinct epithelial gene expression phenotypes in childhood respiratory allergy," European Respiratory Journal, 2012, 39(5):1197-205.
Gorrell et al., "CD26: a multifunctional integral membrane and secreted protein of activated lymphocytes," Scand J Immunol, 2001, 54:249-264.
Gorrell, M., "Dipeptidyl peptidase IV and related enzymes in cell biology and liver disorders," Clin. Sci., 2005, 108, 277-292.
GrubekJaworska et al., "IL-6 and IL-13 in Induced Sputum of COPD and Asthma Patients: Correlation with Respiratory Tests," Respiration, 2012, 84:101-107.
Gupta et al., "Quantitative analysis of high-resolution computed tomography scans in severe asthma subphenotypes," Thorax, 2010, 65(9):775-81.
Gupta et al., "Quantitative computed tomography—derived clusters: Redefining airway remodeling in asthmatic patients," J Allergy Clin Immunol., 2014, 133(3): 729-738.

Haldar, et al., "Mepolizumab and exacerbations of refractory eosinophilic asthma," N Engl J Med., 2009, 360(10):973-84.
Harlow et al., Antibodies: A Laboratory Manual, (Cold Spring Harbor Laboratory Press, 2nd ed. 1988).
Heike et al., "Tissue distribution of the T cell activation antigen Ta1. Serological, immunohistochemical and biochemical investigations," Clin Exp Immunol., 1988, 74:431-434.
Ikushima H, et al., "Soluble CD26/dipeptidyl peptidase IV enhances transendothelial migration via its interaction with mannose 6-phosphate/insulin-like growth factor II receptor," Cell Immunol., 2002, 215(1): 106-10.
International Search Report and Written Opinion for Application No. PCT/US2015/012885 dated Apr. 15, 2015 (13 pages).
Jia, et al., "Periostin is a systemic biomarker of eosinophilic airway inflammation in asthmatic patients," J Allergy Clin. Immunol., 2012, 130:647-654.
Jovani, M., et al., "Anti-IL-13 in inflammatory bowel disease: from the bench to the bedside," Curr Drug Targets, 2013, 12:1444-52.
Juniper et al., "Determining a minimal important change in a disease-specific Quality of Life Questionnaire," J. Clin. Epiderniol., 1994; 47: 81-7.
Juniper et al., "Development and validation of questionnaire to measure asthma control," Eur. Respir. J., 1999, 14:902-7.
Juniper et al., "Identifying 'well-controlled' and 'not well-controlled' asthma using the Asthma Control Questionnaire," Respir. Med., 2006, 100:616-21.
Juniper et al., "Measurement properties and interpretation of three shortened versions of the asthma control questionnaire," Respir. Med., 2005, 99:553-8.
Juniper et al., "Validation of a standardized version of the Asthma Quality of Life Questionnaire," Chest, 1999, 115(5): 1265-70.
Kabat, E. et al., "Sequences of Proteins of Immunological Interest," U.S. Department of Health and Human Services, (1983).
Kanemitsu et al., "Increased periostin associates with greater airflow limitation in patients receiving inhaled corticosteroids," J. Allergy Clin. Immunol., 2013, 132:305-12.
Kilpatrick, K. et al., "Rapid development of affinity matured monoclonal antibodies using RIMMS," Hybridoma, 2009, 16:381-389.
Kioi, M. et al., "Mechanism of action of interleukin-13 antagonist (IL-13E13K) in cells expressing various types of IL-4R," Cell Immunol., 2004, 229:41-51.
Luckow and Summers, "Trends in the Development of Baculovirus Expression Vectors," BioTechnology, 1988, 6:47.
Lun et al., "Increased expression of plasma and CD4+ T lymphocyte costimulatory molecule CD26 in adult patients with allergic asthma," J. Clin. Immunol., 2007, 27:430-437.
Marguet et al., "Enhanced insulin secretion and improved glucose tolerance in mice lacking CD26," Proc Natl Acad Sci USA, 2000, 97(12):6874-9.
McIntosh et al., "Applications of dipeptidyl peptidase IV inhibitors in diabetes mellitus," Int. J. Biochem. Cell Biol., 2006, 38, 860-872.
McKenzie et al., "Structural comparison and chromosomal localization of the human and mouse IL-13 genes," J Immunol, 1993, 150:5436-44.
Mentlein R., "Dipeptidyl-peptidase IV (CD26)—role in the inactivation of regulatory peptides," Regul Pept., 1999, 85(1):9-24.
Metwally et al., "IL-13 gene expression in patients with atopic dermatitis: relation to IgE level and to disease severity," Egypt J. Immunol., 2004, 11:171-7.
Milgrom, H. et al., "Assessing adherence with asthma medication: making the counts count," Ann Allergy Asthma Immunol, 2002, 88:429-31.
Miller et al., "General considerations for lung function testing," Eur. Respir. J., 2005, 26:153-61.
Minty, A. et al., "Interleukin-13 is a new human lymphokine regulating inflammatory and immune responses," Nature, 1993, 362:248-50.
Molica et al., "Serum level of CD26 predicts time treatment in early B-chronic lymphocytic leukemia," European Journal of Haematology, 2009, vol. 83, No. 3, pp. 208-214.
Naidich, et al, Imaging of the Airways—Functional and Radiologic Correlations, 2005.
Oh et al., "IL-13 induces skin fibrosis in atopic dermatitis by thymic stromal lymphopoietin," J Immunol., 2011, 186:7232-42.

(56) References Cited

OTHER PUBLICATIONS

Ohnuma et al, "Role of CD26/dipeptidyl peptidase IV in human T cell activation and function," Front Biosci., 2008, 13:2299-310.

Purwar et al, "IL-13-stimulated human keratinocytes preferentially attract CD4+CCR4+ T cells: possible role in atopic dermatitis," J. Invest. Denn., 2006, 126, 1043- 1051.

Rafii et al., "A Review of Current and Novel Therapies for Idiopathic Pulmonary Fibrosis," J Thorac Dis., 2013, 1:48-73.

Sasaki et al., "Serum level of the periostin, a homologue of an insect cell adhesion molecule, as a prognostic marker in nonsmall cell lung carcinomas," Cancer, 2001, 92:843-848.

Shiobara et al., "The Analysis of Dipeptidyl Peptidase-4 Expressions and Functions in Distal Bronchial Epithelium of Steroid Naive Bronchial Asthma," Am J Respir Crit Care Med, 2014, 189:A4239.

Sidhu et al., "Roles of epithelial cell-derived periostin in TGF-β activation, collagen production, and collagen gel elasticity in asthma," Proc. Natl. Acad. Sci. USA, 2010, 107: 14170-14175.

Takayama et al., "Periostin: a novel component of subepithelialfibrosis of bronchial asthma downstream of IL-4 and IL-13 signals," J Allergy Clin Immunol, 2006, 118:98-104.

Takeshita et al., "Osteoblast-specific factor 2: cloning of a putative bone adhesion protein with homology with the insect protein fasciclin I," Biochem J., 1993, 294:271-278.

Tashkin et al., "Methacholine reactivity predicts changes in lung function over time in smokers with early chronic obstructive pulmonary disease. The Lung Health Study Research Group," Am J Respir Crit Care Med, 1996, 153(6 Pt 1): 1802-11.

Tazawa et al., "Relative importance of IL-4 and IL-13 in lesional skin of atopic dermatitis," Arch. Dermatol. Res., 2004, 295:459-464.

Van Der Pouw Kraan et al., "Chronic obstructive pulmonary disease is associated with the—1055 IL-13 promoter polymorphism," Genes Immun., 2002, 3: 436-9.

Walsh, "Tralokinumab, an anti-IL-13 mAb for the potential treatment of asthma and COPD," Curr. Opin. Investig. Drugs, 2010, 11 :1305-12.

Woodruff et al., "T-helper type 2-driven inflammation defines major subphenotypes of asthma," Am. J. Respir. Crit. Care Med., 2009, 180:388-395.

Yaron et al., "Proline-dependent structural and biological properties of peptides and proteins," Crit. Rev. Biochem. Mol. Biol., 1993, 28, 31-81.

Zhang et al., American Journal of Respiratory and Critical Care Medicine, 2014, 189:A4875.

Zheng et al., "Inducible targeting of IL-13 to the adult lung causes matrix metalloproteinase- and cathepsin-dependent emphysema," J Clin Invest, 2000, 106: 1081-93.

Zhong et al., "An emerging role of dipeptidyl peptidase 4 (DPP4) beyond glucose control: potential implications in cardiovascular disease," Atherosclerosis, 2013, 226:305-314.

\* cited by examiner

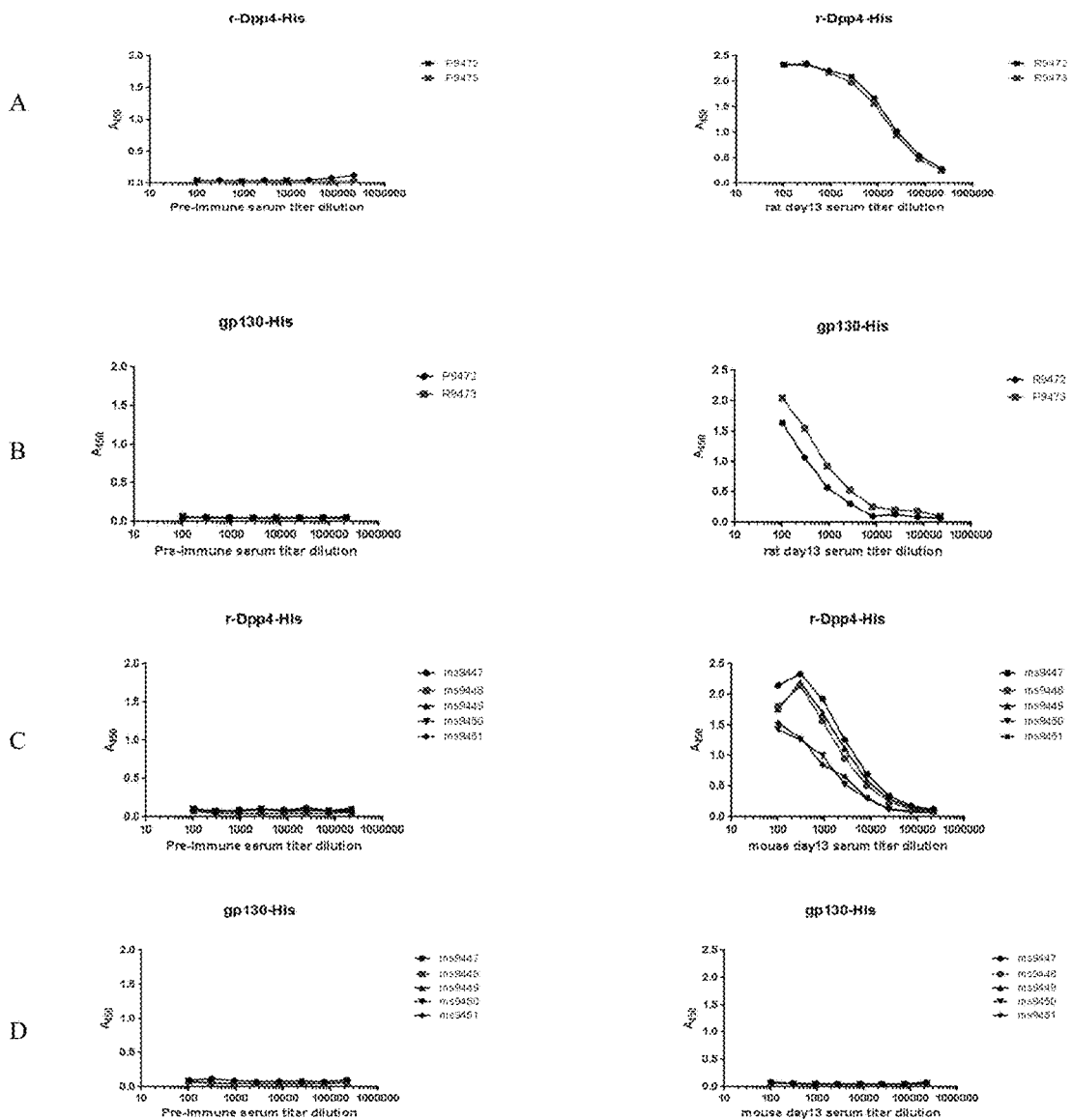
FIG. 2 A-D

SEQUENCE LISTING

```
<160> NUMBER OF SEQ ID NOS: 7

<210> SEQ ID NO 1
<211> LENGTH: 445
<212> TYPE: PRT
<213> ORGANISM: Homo sapiens
<220> FEATURE:
<221> NAME/KEY: misc_feature
<222> LOCATION: (1)..(445)
<223> OTHER INFORMATION: Lebrikizumab Heavy chain

<400> SEQUENCE: 1

Gln Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
```

```
            180                 185                 190
Ser Leu Gly Thr Lys Thr Tyr Thr Cys Asn Val Asp His Lys Pro Ser
            195                 200                 205

Asn Thr Lys Val Asp Lys Arg Val Glu Ser Lys Tyr Gly Pro Pro Cys
        210                 215                 220

Pro Pro Cys Pro Ala Pro Glu Phe Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 2
<211> LENGTH: 218
<212> TYPE: PRT
<213> ORGANISM: Homo sapiens
<220> FEATURE:
<221> NAME/KEY: misc_feature
<222> LOCATION: (1)..(218)
<223> OTHER INFORMATION: Lebrikizumab Light chain

<400> SEQUENCE: 2

Asp Ile Val Met Thr Gln Ser Pro Asp Ser Leu Ser Val Ser Leu Gly
1               5                   10                  15

Glu Arg Ala Thr Ile Asn Cys Arg Ala Ser Lys Ser Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln Gln Asn Asn
                85                  90                  95
```

Glu Asp Pro Arg Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
        130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 3
<211> LENGTH: 122
<212> TYPE: PRT
<213> ORGANISM: Homo sapiens
<220> FEATURE:
<221> NAME/KEY: misc_feature
<222> LOCATION: (1)..(122)
<223> OTHER INFORMATION: Tralokinumab Heavy chain

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Leu Ser Trp Val Arg Gln Ala Pro Gly Gln Gly Leu Glu Trp Met
        35                  40                  45

Gly Trp Ile Ser Ala Asn Asn Gly Asp Thr Asn Tyr Gly Gln Glu Phe
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Ser Ser Ser Ser Trp Ala Arg Trp Phe Phe Asp Leu Trp
            100                 105                 110

Gly Arg Gly Thr Leu Val Thr Val Ser Ser
        115                 120

<210> SEQ ID NO 4
<211> LENGTH: 108
<212> TYPE: PRT
<213> ORGANISM: Homo sapiens
<220> FEATURE:
<221> NAME/KEY: misc_feature
<222> LOCATION: (1)..(108)
<223> OTHER INFORMATION: Tralokinumab Light chain

<400> SEQUENCE: 4

Ser Tyr Val Leu Thr Gln Pro Pro Ser Val Ser Val Ala Pro Gly Lys
1               5                   10                  15

Thr Ala Arg Ile Thr Cys Gly Gly Asn Ile Ile Gly Ser Lys Leu Val
            20                  25                  30

-continued

His Trp Tyr Gln Gln Lys Pro Gly Gln Ala Pro Val Leu Val Ile Tyr
            35                  40                  45

Asp Asp Gly Asp Arg Pro Ser Gly Ile Pro Glu Arg Phe Ser Gly Ser
 50                  55                  60

Asn Ser Gly Asn Thr Ala Thr Leu Thr Ile Ser Arg Val Glu Ala Gly
 65                  70                  75                  80

Asp Glu Ala Asp Tyr Tyr Cys Gln Val Trp Asp Thr Gly Ser Asp Pro
                 85                  90                  95

Val Val Phe Gly Gly Gly Thr Lys Leu Thr Val Leu
                100                 105

<210> SEQ ID NO 5
<211> LENGTH: 766
<212> TYPE: PRT
<213> ORGANISM: Homo sapiens
<220> FEATURE:
<221> NAME/KEY: misc_feature
<222> LOCATION: (1)..(766)
<223> OTHER INFORMATION: DPP4 membrane bound form

<400> SEQUENCE: 5

Met Lys Thr Pro Trp Lys Val Leu Leu Gly Leu Leu Gly Ala Ala Ala
 1               5                   10                  15

Leu Val Thr Ile Ile Thr Val Pro Val Val Leu Leu Asn Lys Gly Thr
                 20                  25                  30

Asp Asp Ala Thr Ala Asp Ser Arg Lys Thr Tyr Thr Leu Thr Asp Tyr
             35                  40                  45

Leu Lys Asn Thr Tyr Arg Leu Lys Leu Tyr Ser Leu Arg Trp Ile Ser
 50                  55                  60

Asp His Glu Tyr Leu Tyr Lys Gln Glu Asn Asn Ile Leu Val Phe Asn
 65                  70                  75                  80

Ala Glu Tyr Gly Asn Ser Ser Val Phe Leu Glu Asn Ser Thr Phe Asp
                 85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Val Phe
        195                 200                 205

Ser Ala Tyr Ser Ala Leu Trp Trp Ser Pro Asn Gly Thr Phe Leu Ala
    210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

Thr Asp Ser Leu Ser Ser Val Thr Asn Ala Thr Ser Ile Gln Ile Thr

```
                    275                 280                 285
Ala Pro Ala Ser Met Leu Ile Gly Asp His Tyr Leu Cys Asp Val Thr
290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
                340                 345                 350

Trp Val Gly Arg Phe Arg Pro Ser Glu Pro His Phe Thr Leu Asp Gly
                355                 360                 365

Asn Ser Phe Tyr Lys Ile Ile Ser Asn Glu Glu Gly Tyr Arg His Ile
                370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                    405                 410                 415

Tyr Ile Ser Asn Glu Tyr Lys Gly Met Pro Gly Gly Arg Asn Leu Tyr
                420                 425                 430

Lys Ile Gln Leu Ser Asp Tyr Thr Lys Val Thr Cys Leu Ser Cys Glu
                435                 440                 445

Leu Asn Pro Glu Arg Cys Gln Tyr Tyr Ser Val Ser Phe Ser Lys Glu
450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
                500                 505                 510

Lys Leu Asp Phe Ile Ile Leu Asn Glu Thr Lys Phe Trp Tyr Gln Met
                515                 520                 525

Ile Leu Pro Pro His Phe Asp Lys Ser Lys Lys Tyr Pro Leu Leu Leu
                530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
                580                 585                 590

Ala Ile Asn Arg Arg Leu Gly Thr Phe Glu Val Glu Asp Gln Ile Glu
                595                 600                 605

Ala Ala Arg Gln Phe Ser Lys Met Gly Phe Val Asp Asn Lys Arg Ile
                610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                    645                 650                 655

Ser Arg Trp Glu Tyr Tyr Asp Ser Val Tyr Thr Glu Arg Tyr Met Gly
                660                 665                 670

Leu Pro Thr Pro Glu Asp Asn Leu Asp His Tyr Arg Asn Ser Thr Val
                675                 680                 685

Met Ser Arg Ala Glu Asn Phe Lys Gln Val Glu Tyr Leu Leu Ile His
                690                 695                 700
```

```
Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
        755                 760                 765
```

<210> SEQ ID NO 6
<211> LENGTH: 728
<212> TYPE: PRT
<213> ORGANISM: Homo sapiens
<220> FEATURE:
<221> NAME/KEY: misc_feature
<222> LOCATION: (1)..(728)
<223> OTHER INFORMATION: DPP4 soluble form

<400> SEQUENCE: 6

```
Ser Arg Lys Thr Tyr Thr Leu Thr Asp Tyr Leu Lys Asn Thr Tyr Arg
1               5                   10                  15

Leu Lys Leu Tyr Ser Leu Arg Trp Ile Ser Asp His Glu Tyr Leu Tyr
            20                  25                  30

Lys Gln Glu Asn Asn Ile Leu Val Phe Asn Ala Glu Tyr Gly Asn Ser
        35                  40                  45

Ser Val Phe Leu Glu Asn Ser Thr Phe Asp Glu Phe Gly His Ser Ile
    50                  55                  60

Asn Asp Tyr Ser Ile Ser Pro Asp Gly Gln Phe Ile Leu Leu Glu Tyr
65                  70                  75                  80

Asn Tyr Val Lys Gln Trp Arg His Ser Tyr Thr Ala Ser Tyr Asp Ile
                85                  90                  95

Tyr Asp Leu Asn Lys Arg Gln Leu Ile Thr Glu Glu Arg Ile Pro Asn
            100                 105                 110

Asn Thr Gln Trp Val Thr Trp Ser Pro Val Gly His Lys Leu Ala Tyr
        115                 120                 125

Val Trp Asn Asn Asp Ile Tyr Val Lys Ile Glu Pro Asn Leu Pro Ser
    130                 135                 140

Tyr Arg Ile Thr Trp Thr Gly Lys Glu Asp Ile Ile Tyr Asn Gly Ile
145                 150                 155                 160

Thr Asp Trp Val Tyr Glu Glu Glu Val Phe Ser Ala Tyr Ser Ala Leu
                165                 170                 175

Trp Trp Ser Pro Asn Gly Thr Phe Leu Ala Tyr Ala Gln Phe Asn Asp
            180                 185                 190

Thr Glu Val Pro Leu Ile Glu Tyr Ser Phe Tyr Ser Asp Glu Ser Leu
        195                 200                 205

Gln Tyr Pro Lys Thr Val Arg Val Pro Tyr Pro Lys Ala Gly Ala Val
    210                 215                 220

Asn Pro Thr Val Lys Phe Phe Val Val Asn Thr Asp Ser Leu Ser Ser
225                 230                 235                 240

Val Thr Asn Ala Thr Ser Ile Gln Ile Thr Ala Pro Ala Ser Met Leu
                245                 250                 255

Ile Gly Asp His Tyr Leu Cys Asp Val Thr Trp Ala Thr Gln Glu Arg
            260                 265                 270

Ile Ser Leu Gln Trp Leu Arg Arg Ile Gln Asn Tyr Ser Val Met Asp
        275                 280                 285
```

```
-continued

Ile Cys Asp Tyr Asp Glu Ser Ser Gly Arg Trp Asn Cys Leu Val Ala
    290                 295                 300

Arg Gln His Ile Glu Met Ser Thr Thr Gly Trp Val Gly Arg Phe Arg
305                 310                 315                 320

Pro Ser Glu Pro His Phe Thr Leu Asp Gly Asn Ser Phe Tyr Lys Ile
                325                 330                 335

Ile Ser Asn Glu Glu Gly Tyr Arg His Ile Cys Tyr Phe Gln Ile Asp
            340                 345                 350

Lys Lys Asp Cys Thr Phe Ile Thr Lys Gly Thr Trp Glu Val Ile Gly
        355                 360                 365

Ile Glu Ala Leu Thr Ser Asp Tyr Leu Tyr Ile Ser Asn Glu Tyr
    370                 375                 380

Lys Gly Met Pro Gly Gly Arg Asn Leu Tyr Lys Ile Gln Leu Ser Asp
385                 390                 395                 400

Tyr Thr Lys Val Thr Cys Leu Ser Cys Glu Leu Asn Pro Glu Arg Cys
                405                 410                 415

Gln Tyr Tyr Ser Val Ser Phe Ser Lys Glu Ala Lys Tyr Tyr Gln Leu
            420                 425                 430

Arg Cys Ser Gly Pro Gly Leu Pro Leu Tyr Thr Leu His Ser Ser Val
        435                 440                 445

Asn Asp Lys Gly Leu Arg Val Leu Glu Asp Asn Ser Ala Leu Asp Lys
    450                 455                 460

Met Leu Gln Asn Val Gln Met Pro Ser Lys Lys Leu Asp Phe Ile Ile
465                 470                 475                 480

Leu Asn Glu Thr Lys Phe Trp Tyr Gln Met Ile Leu Pro Pro His Phe
                485                 490                 495

Asp Lys Ser Lys Lys Tyr Pro Leu Leu Leu Asp Val Tyr Ala Gly Pro
            500                 505                 510

Cys Ser Gln Lys Ala Asp Thr Val Phe Arg Leu Asn Trp Ala Thr Tyr
        515                 520                 525

Leu Ala Ser Thr Glu Asn Ile Ile Val Ala Ser Phe Asp Gly Arg Gly
    530                 535                 540

Ser Gly Tyr Gln Gly Asp Lys Ile Met His Ala Ile Asn Arg Arg Leu
545                 550                 555                 560

Gly Thr Phe Glu Val Glu Asp Gln Ile Glu Ala Ala Arg Gln Phe Ser
                565                 570                 575

Lys Met Gly Phe Val Asp Asn Lys Arg Ile Ala Ile Trp Gly Trp Ser
            580                 585                 590

Tyr Gly Gly Tyr Val Thr Ser Met Val Leu Gly Ser Gly Ser Gly Val
        595                 600                 605

Phe Lys Cys Gly Ile Ala Val Ala Pro Val Ser Arg Trp Glu Tyr Tyr
    610                 615                 620

Asp Ser Val Tyr Thr Glu Arg Tyr Met Gly Leu Pro Thr Pro Glu Asp
625                 630                 635                 640

Asn Leu Asp His Tyr Arg Asn Ser Thr Val Met Ser Arg Ala Glu Asn
                645                 650                 655

Phe Lys Gln Val Glu Tyr Leu Leu Ile His Gly Thr Ala Asp Asp Asn
            660                 665                 670

Val His Phe Gln Gln Ser Ala Gln Ile Ser Lys Ala Leu Val Asp Val
        675                 680                 685

Gly Val Asp Phe Gln Ala Met Trp Tyr Thr Asp Glu Asp His Gly Ile
    690                 695                 700

Ala Ser Ser Thr Ala His Gln His Ile Tyr Thr His Met Ser His Phe
```

Ile Lys Gln Cys Phe Ser Leu Pro
            725

<210> SEQ ID NO 7
<211> LENGTH: 3913
<212> TYPE: DNA
<213> ORGANISM: Homo sapiens
<220> FEATURE:
<221> NAME/KEY: misc_feature
<222> LOCATION: (1)..(766)
<223> OTHER INFORMATION: DPP4 membrane bound form (full sequence), cDNA

<400> SEQUENCE: 7

| | | | | | |
|---|---|---|---|---|---|
| ctttcactgg | caagagacgg | agtcctgggt | ttcagttcca | gttgcctgcg | gtgggctgtg | 60 |
| tgagtttgcc | aaagtcccct | gccctctctg | ggtctcggtt | ccctcgcctg | tccacgtgag | 120 |
| gttggaggag | ctgaacgccg | acgtcatttt | tagctaagag | ggagcagggt | ccccgagtcg | 180 |
| ccggcccagg | gtctgcgcat | ccgaggccgc | gcgcccttc | cctccccca | cggctcctcc | 240 |
| gggcccccgca | ctctgcgccc | cggctgccgc | ccagcgccct | acaccgccct | caggggggccc | 300 |
| tcgcgggctc | ccccggccg | ggatgccagt | gccccgcgcc | acgcgcgcct | gctcccgcgc | 360 |
| cgcctgccct | gcagcctgcc | cgcggcgcct | ttatacccag | cgggctcggc | gctcactaat | 420 |
| gtttaactcg | gggccgaaac | ttgccagcgg | cgagtgactc | caccgcccgg | agcagcggtg | 480 |
| caggacgcgc | gtctccgccg | cccgcggtga | cttctgcctg | cgctccttct | ctgaacgctc | 540 |
| acttccgagg | agacgccgac | gatgaagaca | ccgtggaagg | ttcttctggg | actgctgggt | 600 |
| gctgctgcgc | ttgtcaccat | catcaccgtg | cccgtggttc | tgctgaacaa | aggcacagat | 660 |
| gatgctacag | ctgacagtcg | caaaacttac | actctaactg | attacttaaa | aaatactat | 720 |
| agactgaagt | tatactcctt | aagatggatt | tcagatcatg | aatatctcta | caaacaagaa | 780 |
| aataatatct | tggtattcaa | tgctgaatat | ggaaacagct | cagtttttct | tggagaacagt | 840 |
| acatttgatg | agtttggaca | ttctatcaat | gattattcaa | tatctcctga | tgggcagttt | 900 |
| attctcttag | aatacaacta | cgtgaagcaa | tggaggcatt | cctacacagc | ttcatatgac | 960 |
| atttatgatt | taaataaaag | gcagctgatt | acagaagaga | ggattccaaa | caacacacag | 1020 |
| tgggtcacat | ggtcaccagt | gggtcataaa | ttggcatatg | tttggaacaa | tgacatttat | 1080 |
| gttaaaattg | aaccaaattt | accaagttac | agaatcacat | ggacggggaa | agaagatata | 1140 |
| atatataatg | gaataactga | ctgggtttat | gaagaggaag | tcttcagtgc | ctactctgct | 1200 |
| ctgtggtggt | ctccaaacgg | cacttttta | gcatatgccc | aatttaacga | cacagaagtc | 1260 |
| ccacttattg | aatactcctt | ctactctgat | gagtcactgc | agtacccaaa | gactgtacgg | 1320 |
| gttccatatc | caaaggcagg | agctgtgaat | ccaactgtaa | agttctttgt | tgtaaataca | 1380 |
| gactctctca | gctcagtcac | caatgcaact | tccatacaaa | tcactgctcc | tgcttctatg | 1440 |
| ttgataggg | atcactactt | gtgtgatgtg | acatgggcaa | cacaagaaag | aatttctttg | 1500 |
| cagtggctca | ggaggattca | gaactattcg | gtcatggata | tttgtgacta | tgatgaatcc | 1560 |
| agtggaagat | ggaactgctt | agtggcacgg | caacacattg | aaatgagtac | tactggctgg | 1620 |
| gttggaagat | ttaggccttc | agaacctcat | tttacccttg | atggtaatag | cttctacaag | 1680 |
| atcatcagca | atgaagaagg | ttacagacac | atttgctatt | ccaaataga | taaaaagac | 1740 |
| tgcacattta | ttacaaaagg | cacctgggaa | gtcatcggga | tagaagctct | aaccagtgat | 1800 |
| tatctatact | acattagtaa | tgaatataaa | ggaatgccag | gaggaaggaa | tctttataaa | 1860 |

```
atccaactta gtgactatac aaaagtgaca tgcctcagtt gtgagctgaa tccggaaagg    1920
tgtcagtact attctgtgtc attcagtaaa gaggcgaagt attatcagct gagatgttcc    1980
ggtcctggtc tgcccctcta tactctacac agcagcgtga atgataaagg gctgagagtc    2040
ctggaagaca attcagcttt ggataaaatg ctgcagaatg tccagatgcc ctccaaaaaa    2100
ctggacttca ttattttgaa tgaaacaaaa ttttggtatc agatgatctt gcctcctcat    2160
tttgataaat ccaagaaata tcctctacta ttagatgtgt atgcaggccc atgtagtcaa    2220
aaagcagaca ctgtcttcag actgaactgg gccacttacc ttgcaagcac agaaaacatt    2280
atagtagcta gctttgatgg cagaggaagt ggttaccaag gagataagat catgcatgca    2340
atcaacagaa gactgggaac atttgaagtt gaagatcaaa ttgaagcagc cagacaattt    2400
tcaaaaatgg gatttgtgga caacaaacga attgcaattt ggggctggtc atatggaggg    2460
tacgtaacct caatggtcct gggatcggga agtggcgtgt tcaagtgtgg aatagccgtg    2520
gcgcctgtat cccggtggga gtactatgac tcagtgtaca cagaacgtta catgggtctc    2580
ccaactccag aagacaacct tgaccattac agaaattcaa cagtcatgag cagagctgaa    2640
aattttaaac aagttgagta cctccttatt catggaacag cagatgataa cgttcacttt    2700
cagcagtcag ctcagatctc caaagccctg gtcgatgttg gagtggattt ccaggcaatg    2760
tggtatactg atgaagacca tggaatagct agcagcacag cacaccaaca tatatatacc    2820
cacatgagcc acttcataaa acaatgtttc tctttacctt agcacctcaa aataccatgc    2880
catttaaagc ttattaaaac tcattttgt tttcattatc tcaaaactgc actgtcaaga    2940
tgatgatgat ctttaaaata cacactcaaa tcaagaaact taaggttacc tttgttccca    3000
aatttcatac ctatcatctt aagtagggac ttctgtcttc acaacagatt attaccttac    3060
agaagtttga attatccggt cgggttttat tgtttaaaat catttctgca tcagctgctg    3120
aaacaacaaa taggaattgt ttttatggag gctttgcata gattccctga gcaggatttt    3180
aatcttttc taactggact ggttcaaatg ttgttctctt cttaaagg atggcaagat    3240
gtgggcagtg atgtcactag gcagggaca ggataagagg gattagggag agaagatagc    3300
agggcatggc tgggaaccca agtccaagca taccaacacg agcaggctac tgtcagctcc    3360
cctcggagaa gagctgttca cagccagact ggcacagttt tctgagaaag actattcaaa    3420
cagtctcagg aaatcaaata tgcaaagcac tgacttctaa gtaaaaccac agcagttgaa    3480
aagactccaa agaaatgtaa gggaaactgc cagcaacgca ggcccccagg tgccagttat    3540
ggctataggt gctacaaaaa cacagcaagg gtgatgggaa agcattgtaa atgtgctttt    3600
aaaaaaaaat actgatgttc ctagtgaaag aggcagcttg aaactgagat gtgaacacat    3660
cagcttgccc tgttaaaaga tgaaatatt tgtatcacaa atcttaactt gaaggagtcc    3720
ttgcatcaat ttttcttatt tcatttcttt gagtgtctta attaaaagaa tattttaact    3780
tccttggact cattttaaaa aatggaacat aaaatacaat gttatgtatt attattccca    3840
ttctacatac tatggaattt ctcccagtca tttaataaat gtgccttcat tttttcagaa    3900
aaaaaaaaaa aaa                                                      3913
```

ASSAY TO DETECT HUMAN DPP-4

This application claims benefit under 35 U.S.C. § 119(e) of the following U.S. Provisional Application Nos. 62/101,697 filed Jan. 9, 2015. The above listed application is incorporated by reference herein in its entirety for all purposes.

The content of the electronically submitted sequence listing in ASCII text file (Name DPP4-100P1_sequence_listing.txt; Size: 26,741 bytes; and Date of Creation: Dec. 15, 2014) filed with the application is incorporated herein by reference in its entirety.

BACKGROUND

Dipeptidyl Peptidase IV (DPP-4) (also known as CD26 or adenosine deaminase binding protein) is a type II transmembrane serine protease in the prolyl oligopeptidase family that catalyzes the hydrolysis of N-terminal dipeptides from the N-terminus of polypeptides having a proline or alanine in position 2 (Enzyme Commission (EC) Number 3.4.14.5 (BRENDA I IUBMB)). A number of chemokine and peptide hormones including GLP-1, GLP-2, gastric inhibitory polypeptide (GIP), pituitary adenylate cyclase-activating polypeptide (PACAP) and neuropeptide Y are cleaved and inactivated by DPP-4. See, e.g., Yaron A., Naider F. Crit. Rev. Biochem. Mol. Biol. 28, 31-81 (1993); Mentlein R. Regul Pept. 85(1):9-24 (1999). As a result, DPP-4 regulates glucose metabolism, appetite and pain regulation though its ability to inhibit chemokine and peptide hormones.

In addition to its role as a regulatory protease, DPP-4 also binds several molecules and induces intracellular signal transduction. In particular, DPP-4 induces T-cell co-stimulation/proliferation and lymphocyte-epithelial cell adhesion by binding to several ligands including adenosine deaminase (ADA). See, e.g., Gines et al., Biochem. J. 361:203-209 (2002). DPP-4 has also been reported to enhance T-cell maturation and migration, cytokine secretion, antibody production, immunoglobulin isotype switching of B cells, and activation of cytotoxic T cells. Ohnuma et. al., Front Biosci. 13:2299-310 (2008).

DPP-4 is a 110 kDa glycoprotein, encoded by a gene located on chromosome 2 (2q24.3) (Abbott et al. Immunogenetics. 40(5):331-8 (1994)), and functions as a homodimer consisting of 766 amino acids. Each monomer consists of two domains: an alpha/beta hydrolase domain and an eight-blade beta-propeller domain. DPP-4 is widely expressed in several tissues including liver, lung, kidney, epithelial cells and lymphocytes. Heike et al. Clin Exp Immunol. 74:431-434 91988); Gorrell et al., Scand J Immunol. 54:249-264 (2001). Upon T cell activation, DPP-4 expression is up-regulated on resting T cells. A soluble, active form of DPP-4 containing most of the extracellular domain (residues 39-766) including the key catalytic domain, has also been observed. Ikushima H, et al. Cell Immunol. 215(1):106-10 (2002).

DPP-4 gene knock out mice show improved glucose tolerance with oral glucose loading, increased insulin and GLP-1 activity; resistance to diet-induced obesity; and increased insulin sensitivity following high-fat diets. Marguet al., Proc Natl Acad Sci USA. 97(12):6874-9 (2000); Conarello et al., Proc Natl Acad Sci USA. 100(11):6825-30 (2003). In addition to its role in metabolic disorders and glycemic control, DPP-4 has also been implicated in controlling immune function, cell migration, entry of viruses into cells, cancer metastasis and inflammation. See, e.g., Aytac et al., Curr Drug Targets Immune Endocr Metabol Disord 4(1):11-8 (2004).

More recently, DPP-4 expression has been reported to be highly induced by Interleukin-13 (IL-13). See, e.g., Zhang et al., Am J Respir Crit Care Med 189:A4875 (2014); Shiobara et al., Am J Respir Crit Care Med 189:A4239 (2014); Brightling et al., Am J Respir Crit Care Med 189:A6670 (2014); U.S. Provisional Application No. 61/931,878, filed Jan. 27, 2014; and U.S. Provisional Application No. 61/990,932, filed May 9, 2014, each herein incorporated by reference in its entirety for all purposes. IL-13 is a 114 amino acid cytokine with an unmodified molecular mass of approximately 12 kDa. McKenzie, A. N., et al. J Immunol, 1993. 150:5436-44; Minty, A., et al. Nature, 1993. 362:248-50. IL-13 levels have been shown to correlate with disease severity in a number of diseases or disorders including, but not limited to, asthma, chronic obstructive pulmonary disease, idiopathic pulmonary fibrosis, and atopic dermatitis. For example, in asthmatics and rodent models of allergic inflammation elevated IL-13 levels have been reported to correlate with disease severity (see U.S. Pat. Appl. Publ. No. 2012-0052060, published Mar. 1, 2012, and incorporated herein by reference in its entirety).

Chronic obstructive pulmonary disease (COPD) includes patient populations with varying degrees of chronic bronchitis, small airway disease, and emphysema, and is characterized by progressive irreversible lung function decline that responds poorly to current asthma based therapy. Zheng et al (J Clin Invest, 2000. 106:1081-93) demonstrated that overexpression of IL-13 in the mouse lung caused emphysema, elevated mucus production, and inflammation, reflecting aspects of human COPD. The signs are therefore that IL-13 plays an important role in the pathogenesis of COPD, particularly in patients with asthma-like features.

IL-13 can also play a role in the pathogenesis of inflammatory bowel disease, and has been associated with fibrotic conditions, such as idiopathic pulmonary fibrosis (IPF). See, e.g., Jovani, M., et al. Curr Drug Targets. 2013.12:1444-52; and Rafii, R., et al. J Thorac Dis. 2013. 1:48-73

Atopic dermatitis is a common chronic inflammatory skin disease that is often associated with other atopic disorders such as allergic rhinitis and asthma (Bieber, New England Journal of Medicine, 2008, 358: 1483-1494). Upregulation of IL-13 mRNA has been observed in subacute and chronic lesions of atopic dermatitis (Tazawa et al., Arch. Dermatol. Res., 2004, 295:459-464; Purwar et al, J. Invest. Derm., 2006, 126, 1043-1051; Oh et al., J Immunol., 2011, 186: 7232-42).

Elevated DPP-4 levels have been observed in asthma, COPD and AD patients (see, e.g., U.S. Provisional Application No. 61/931,878, filed Jan. 27, 2014; and U.S. Provisional Application No. 61/990,932, filed May 9, 2014, each incorporated herein by reference in its entirety). In addition, in a phase 2B clinical study involving asthma patients, high serum DPP-4 levels predicted improved response rates in patients treated with an IL-13 antibody antagonist (tralokinumab) identifying DPP-4 as a predictive biomarker for IL-13-mediated disease or disorders including an IL-13-mediated pulmonary disease or disorder (e.g., asthma, IPF or COPD) or an IL-13-mediated chronic inflammatory skin disease or disorder (e.g., atopic dermatitis). See Brightling et al., Am J Respir Crit Care Med 189:A6670 (2014); and U.S. Provisional Application No. 61/931,878, filed Jan. 27, 2014; and U.S. Provisional Application No. 61/990,932, filed May 9, 2014, each herein incorporated by reference in its entirety. Thus, while increased DPP-4 levels are known to correlate with certain IL-13-mediated diseases or disorders and DPP-4 serum levels are known to predict patient response to anti-IL-13 therapy, there remains a need for specific and sensitive assays to measure the amount and/or determine changes in DPP-4 levels in patients, including, but not limited to, patients suffering from an IL-13-mediated disease or disorder. Although there are commercially available reagents which could be used to measure serum DPP-4 levels in patients, these commercially available reagents or kits rely on polyclonal antibodies, which not only introduce assay variations due to lot to lot differences and/or are not very sensitive. Accordingly, there still remains a need for specific and sensitive antibodies, reagents and/or immunoassays to measure the amount and/or determine changes in DPP-4 levels in patients.

BRIEF SUMMARY

This disclosure provides anti-dipeptidyl peptidase-4 (DPP-4) antibodies that can be used, e.g., in diagnostic assays to determine DPP-4 levels in a subject. Exemplary anti-DPP-4 antibodies of the disclosure include: (1) mouse monoclonal antibody m3B7.6 produced by a hybridoma deposited on Jan. 8, 2015 at the American Type Culture Collection (ATCC), 10801 University Boulevard, Manassas, Va. 20110-2209, under the provisions of the Budapest Treaty on the International Recognition of the Deposit of Microorganisms for the Purpose of Patent Procedures, and assigned ATCC accession number PTA-121870; (2) mouse monoclonal antibody m5B7.7 produced by a hybridoma deposited on Jan. 8, 2015 at the American Type Culture Collection (ATCC), 10801 University Boulevard, Manassas, Va. 20110-2209, under the provisions of the Budapest Treaty on the International Recognition of the Deposit of Microorganisms for the Purpose of Patent Procedures, and assigned ATCC accession number PTA-121871; (3) rat monoclonal antibody R11A2.15 produced by a hybridoma deposited on Jan. 8, 2015 at the American Type Culture Collection (ATCC), 10801 University Boulevard, Manassas, Va. 20110-2209, under the provisions of the Budapest Treaty on the International Recognition of the Deposit of Microorganisms for the Purpose of Patent Procedures, and assigned ATCC accession number PTA-121872; and (4) rat monoclonal antibody R11A9.11 produced by a hybridoma deposited on Jan. 8, 2015 at the American Type Culture Collection (ATCC), 10801 University Boulevard, Manassas, Va. 20110-2209, under the provisions of the Budapest Treaty on the International Recognition of the Deposit of Microorganisms for the Purpose of Patent Procedures, and assigned ATCC accession number PTA-121873.

In certain aspects the disclosure provides an isolated antibody or antigen-binding fragment, variant, or derivative thereof, or two or more such antibodies, where the antibody or antibodies competitively inhibit binding of and/or bind to the same DPP-4 epitope as: (1) mouse monoclonal antibody m3B7.6 produced from a hybridoma deposited at the ATCC under Deposit No. PTA-121870, (2) mouse monoclonal antibody m5B7.7 produced from a hybridoma deposited at the ATCC under Deposit No. PTA-121871, (3) rat monoclonal antibody R11A2.15 produced from a hybridoma deposited at the ATCC under Deposit No. PTA-121872, or (4) rat monoclonal antibody R11A9.11 produced from a hybridoma deposited at the ATCC under Deposit No. PTA-121873, or any combination thereof.

In certain aspects, the disclosure provides an isolated antibody or antigen-binding fragment, variant, or derivative thereof that binds DPP-4, which includes a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, where the CDRs of the isolated antibody, or fragment, variant, or derivative thereof are identical to the CDRs of mouse monoclonal antibody m3B7.6 produced from a hybridoma deposited at the ATCC under Deposit No. PTA-121870, mouse monoclonal antibody m5B7.7 produced from a hybridoma deposited at the ATCC under Deposit No. PTA-121871, rat monoclonal antibody R11A2.15 produced from a hybridoma deposited at the ATCC under Deposit No. PTA-121872, or rat monoclonal antibody R11A9.11 produced from a hybridoma deposited at the ATCC under Deposit No. PTA-121873.

In certain aspects, the antibody or antigen-binding fragment, variant, or derivative thereof provided by this disclosure can include a VH and a VL identical to the VH and VL of mouse monoclonal antibody m3B7.6 produced from a hybridoma deposited at the ATCC under Deposit No. PTA-121870, mouse monoclonal antibody m5B7.7 produced from a hybridoma deposited at the ATCC under Deposit No. PTA-121871, rat monoclonal antibody R11A2.15 produced from a hybridoma deposited at the ATCC under Deposit No. PTA-121872, or rat monoclonal antibody R11A9.11 produced from a hybridoma deposited at the ATCC under Deposit No. PTA-121873.

In certain aspects the disclosure provides an antigen-binding antibody fragment as described above. In certain aspects the antibody fragment can be a Fab fragment, a Fab' fragment, a F(ab')2 fragment, a Fv fragment, or a single chain antibody molecule.

The disclosure further provides a hybridoma deposited at the ATCC under Deposit No. 121870, a hybridoma deposited at the ATCC under Deposit No. 121871, a hybridoma deposited at the ATCC under Deposit No. 121872, a hybridoma deposited at the ATCC under Deposit No. 121873, and/or a combination thereof. In certain aspects the disclosure provides an antibody-producing cell culture that includes a hybridoma deposited at the ATCC under Deposit No. 121870, a hybridoma deposited at the ATCC under Deposit No. 121871, a hybridoma deposited at the ATCC under Deposit No. 121872, a hybridoma deposited at the ATCC under Deposit No. 121873, and/or a combination thereof. In another aspect the disclosure provides an isolated antibody or antigen-binding fragment, variant, or derivative thereof produced by the hybridoma as provided herein or the antibody-producing cell culture as provided herein.

In certain aspects, the antibody, or fragment, variant, or derivative thereof provided by the disclosure, or the antibody produced by the hybridoma or the cell culture provided by the disclosure, or a fragment, variant, or derivative thereof (including, e.g., antibodies m3B7.6, m5B7.7, R11A2.15, or R11A9.11), further includes a heterologous polypeptide fused thereto. For example, in certain aspects, the heterologous polypeptide is a stabilizing polypeptide, a tag, a label, or a combination thereof.

In certain aspects, the antibody, or fragment, variant, or derivative thereof provided by the disclosure, or the antibody produced by the hybridoma or the cell culture provided by the disclosure, or a fragment, variant, or derivative thereof (including, e.g., antibodies m3B7.6, m5B7.7, R11A2.15, or R11A9.11), is conjugated to a heterologous moiety. In certain aspects, the heterologous moiety includes one or more of: a peptide, a protein, an enzyme, a lipid, a heterologous antibody or fragment thereof, a detectable label, or polyethylene glycol (PEG). In certain aspects, the heterologous moiety is, e.g., biotin, or a ruthenium chelate.

The disclosure further provides a composition that includes the antibody, or fragment, variant, or derivative thereof as provided by the disclosure, and/or the antibody produced by the hybridoma or the cell culture provided by the disclosure, or a fragment, variant, or derivative thereof (including, e.g., antibodies m3B7.6, m5B7.7, R11A2.15, and/or R11A9.11). In certain aspects, the composition includes a combination of at least two such antibodies.

In another aspect, the disclosure provides an isolated polynucleotide that includes a nucleic acid molecule encoding an antibody, or a subunit, fragment, variant, or derivative thereof as provided by the disclosure, or the antibody or fragment thereof produced by the hybridoma or the cell culture provided by the disclosure, or a subunit, fragment, variant, or derivative thereof (including, e.g., antibodies m3B7.6, m5B7.7, R11A2.15, or R11A9.11). The disclosure further provides a vector that includes the polynucleotide as provided.

In certain aspects the disclosure provides a composition that includes two or more nucleic acid molecules encoding the antibody, or a fragment, variant, or derivative thereof as provided by the disclosure, or the antibody or fragment thereof produced by the hybridoma or the cell culture provided by the disclosure, or a fragment, variant, or derivative thereof (including, e.g., antibodies m3B7.6, m5B7.7, R11A2.15, or R11A9.11). In certain aspects the two or more nucleic acid molecules are situated in the same vector. The disclosure further provides the vector that includes the two or more nucleic acid molecules as provided, situated in the same vector. In certain aspects, the two or more nucleic acid molecules are situated in at least two separate vectors. The disclosure further provides the two separate vectors.

The disclosure further provides an isolated host cell that includes the provided vector, or the two or more provided vectors. The disclosure further provides a method of making an anti-DPP-4 antibody, or a subunit, fragment, variant, or derivative thereof as provided by the disclosure, or the antibody produced by the hybridoma or the cell culture provided by the disclosure, or a subunit, fragment, variant, or derivative thereof (including, e.g., antibodies m3B7.6, m5B7.7, R11A2.15, and/or R11A9.11), where the method includes (a) culturing the provided host cell, and (b) recovering the antibody, subunit, fragment, or derivative thereof.

In another aspect, the disclosure provides a kit for measuring DPP-4 levels in a sample, where the kit includes the antibody, or fragment, variant, or derivative thereof as provided by the disclosure, or the antibody produced by the hybridoma or the cell culture provided by the disclosure, or a fragment, variant, or derivative thereof (including, e.g., antibodies m3B7.6, m5B7.7, R11A2.15, or R11A9.11). In certain aspects, the kit includes at least two such antibodies, or fragments, variants, or derivatives thereof. The kit can further include a solid support and/or detection reagents. In certain aspects, one of the at least two antibodies or fragments, variants, or derivatives thereof can be a capture antibody, or fragment, variant, or derivative thereof, and one of the at least two antibodies or fragments, variants, or derivatives thereof can be a detection antibody, or fragment, variant, or derivative thereof. In certain aspects the detection antibody can include a detectable label, e.g., the detectable label can be biotin and the kit can include detection reagents such as a streptavidin-horse radish peroxidase (HRP) conjugate and a colorimetric substrate for HRP, or the detectable label can be a ruthenium chelate. In certain aspects:

The capture antibody can be mouse monoclonal antibody m3B7.6 as produced from a hybridoma deposited at the ATCC under Deposit No. PTA-121870, or an antigen-binding fragment, variant, or derivative thereof and the detection antibody can be rat monoclonal antibody R11A2.15 as produced from a hybridoma deposited at the ATCC under Deposit No. PTA-121872 or an antigen-binding fragment, variant, or derivative thereof;

The capture antibody can be mouse monoclonal antibody m3B7.6 as produced from a hybridoma deposited at the ATCC under Deposit No. PTA-121870, or an antigen-binding fragment, variant, or derivative thereof and the detection antibody can be rat monoclonal antibody R11A9.11 as produced from a hybridoma deposited at the ATCC under Deposit No. PTA-121873 or an antigen-binding fragment, variant, or derivative thereof;

The capture antibody can be mouse monoclonal antibody m5B7.7 as produced from a hybridoma deposited at the ATCC under Deposit No. PTA-121871 or an antigen-binding fragment, variant, or derivative thereof and the detection antibody can be rat monoclonal antibody R11A2.15 as produced from a hybridoma deposited at the ATCC under Deposit No. PTA-121872 or an antigen-binding fragment, variant, or derivative thereof;

The capture antibody can be mouse monoclonal antibody m5B7.7 as produced from a hybridoma deposited at the ATCC under Deposit No. PTA-121871 or an antigen-binding fragment, variant, or derivative thereof and the detection antibody can be rat monoclonal antibody R11A9.11 as produced from a hybridoma deposited at the ATCC under Deposit No. PTA-121873 or an antigen-binding fragment, variant, or derivative thereof;

The capture antibody can be rat monoclonal antibody R11A2.15 as produced from a hybridoma deposited at the ATCC under Deposit No. PTA-121872 or an antigen-binding fragment, variant, or derivative thereof and the detection antibody can be mouse monoclonal antibody m3B7.6 as produced from a hybridoma deposited at the ATCC under Deposit No. PTA-121870, or an antigen-binding fragment, variant, or derivative thereof;

The capture antibody can be rat monoclonal antibody R11A2.15 as produced from a hybridoma deposited at the ATCC under Deposit No. PTA-121872 or an antigen-binding fragment, variant, or derivative thereof and the detection antibody can be mouse monoclonal antibody m5B7.7 as produced from a hybridoma deposited at the ATCC under Deposit No. PTA-121871 or an antigen-binding fragment, variant, or derivative thereof;

The capture antibody can be rat monoclonal antibody R11A9.11 as produced from a hybridoma deposited at the ATCC under Deposit No. PTA-121873 or an antigen-binding fragment, variant, or derivative thereof and the detection antibody can be mouse monoclonal antibody m3B7.6 as produced from a hybridoma deposited at the ATCC under Deposit No. PTA-121870, or an antigen-binding fragment, variant, or derivative thereof; and/or The capture antibody can be rat monoclonal antibody R11A9.11 as produced from a hybridoma deposited at the ATCC under Deposit No. PTA-121873 or an antigen-binding fragment, variant, or derivative thereof and the detection antibody can be mouse monoclonal antibody m5B7.7 as produced from a hybridoma deposited at the ATCC under Deposit No. PTA-121871 or an antigen-binding fragment, variant, or derivative thereof.

The disclosure further provides an immunoassay for detecting DPP-4 levels in one or more samples, where the immunoassay includes the use of at least two anti-DPP-4 antibodies or antigen-binding fragments, variants, or derivatives thereof, where one of the anti-DPP-4 antibodies can be an isolated antibody or antigen-binding fragment, variant, or derivative thereof that competitively inhibits binding of and/or binds to the same DPP-4 epitope as mouse monoclonal antibody m3B7.6 produced from a hybridoma deposited at the ATCC under Deposit No. PTA-121870, or mouse monoclonal antibody m5B7.7 produced from a hybridoma deposited at the ATCC under Deposit No. PTA-121871; and where one of the anti-DPP-4 antibodies comprises an isolated antibody or antigen-binding fragment, variant, or derivative thereof that competitively inhibits binding of and/or binds to the same DPP-4 epitope as rat monoclonal antibody R11A2.15 produced from a hybridoma deposited at the ATCC under Deposit No. PTA-121872 or rat monoclonal antibody R11A9.11 produced from a hybridoma deposited at the ATCC under Deposit No. PTA-121873.

In certain aspects, the immunoassay includes the use of at least two anti-DPP-4 antibodies or antigen-binding fragments, variants, or derivatives thereof, where one of the anti-DPP-4 antibodies can be an isolated antibody or antigen-binding fragment, variant, or derivative thereof that includes VH with three heavy chain CDRs VHCDR1, VHCDR2 and VHCDR3, and VL with three light chain CDRs VLCDR1, VLCDR2, and VLCDR3, where the CDRs of the isolated antibody, or fragment, variant, or derivative thereof are identical to the CDRs of mouse monoclonal antibody m3B7.6 produced from a hybridoma deposited at the ATCC under Deposit No. PTA-121870, or mouse monoclonal antibody m5B7.7 produced from a hybridoma deposited at the ATCC under Deposit No. PTA-121871; and where one of the two or more anti-DPP-4 antibodies can be an isolated antibody or antigen-binding fragment, variant, or derivative thereof that includes a VH with three heavy chain CDRs VHCDR1, VHCDR2 and VHCDR3, and VL with three light chain CDRs VLCDR1, VLCDR2, and VLCDR3, where the CDRs of the isolated antibody, or fragment, variant, or derivative thereof are identical to the CDRs of rat monoclonal antibody R11A2.15 produced from a hybridoma deposited at the ATCC under Deposit No. PTA-121872, or rat monoclonal antibody R11A9.11 produced from a hybridoma deposited at the ATCC under Deposit No. PTA-121873.

In certain aspects, the immunoassay includes the use of at least two anti-DPP-4 antibodies or antigen-binding fragments, variants, or derivatives thereof, where one of the two or more anti-DPP-4 antibodies can be an isolated antibody or antigen-binding fragment, variant, or derivative thereof that includes a VH and a VL identical to the VH and VL of mouse monoclonal antibody m3B7.6 produced from a hybridoma deposited at the ATCC under Deposit No. PTA-121870, or mouse monoclonal antibody m5B7.7 produced from a hybridoma deposited at the ATCC under Deposit No. PTA-121871; and where one of the two or more anti-DPP-4 antibodies can be an isolated antibody or antigen-binding fragment, variant, or derivative thereof that includes a VH and a VL identical to the VH and VL of rat monoclonal antibody R11A2.15 produced from a hybridoma deposited at the ATCC under Deposit No. PTA-121872, or rat monoclonal antibody R11A9.11 produced from a hybridoma deposited at the ATCC under Deposit No. PTA-121873.

In certain aspects, the immunoassay can be a sandwich immunoassay that includes use of a first anti-DPP-4 "capture" antibody or antigen-binding fragment thereof attached to a solid support, and a second anti-DPP-4 "detection" antibody or antigen-binding fragment thereof (including, e.g., antibodies m3B7.6, m5B7.7, R11A2.15, and/or R11A9.11). For example, the immunoassay can include attaching a capture antibody or antigen-binding fragment thereof to a solid support; applying the test sample or a control sample under conditions sufficient to allow DPP-4, if present in the sample, to bind to the capture antibody or antigen-binding fragment thereof; applying the detection antibody or antigen-binding fragment thereof under conditions sufficient to allow binding to DPP-4 already bound to the capture antibody or antigen-binding fragment thereof; and measuring the amount of detection antibody or antigen-binding fragment thereof bound to DPP-4. In certain aspects the detection antibody can include a detectable label, e.g., the detectable label can be biotin and the kit can include detection reagents such as a streptavidin-horse radish peroxidase (HRP) conjugate and a colorimetric substrate for HRP, or the detectable label can be a ruthenium chelate.

In certain aspects the immunoassay can include the use of a capture antibody and a detection antibody where:

The capture antibody is mouse monoclonal antibody m3B7.6 as produced from a hybridoma deposited at the ATCC under Deposit No. PTA-121870 or an antigen-binding fragment, variant, or derivative thereof and the detection antibody is rat monoclonal antibody R11A2.15 as produced from a hybridoma deposited at the ATCC under Deposit No. PTA-121872 or an antigen-binding fragment, variant, or derivative thereof;

The capture antibody is mouse monoclonal antibody m3B7.6 as produced from a hybridoma deposited at the ATCC under Deposit No. PTA-121870 or an antigen-binding fragment, variant, or derivative thereof and the detection antibody is rat monoclonal antibody R11A9.11 as produced from a hybridoma deposited at the ATCC under Deposit No. PTA-121873 or an antigen-binding fragment, variant, or derivative thereof;

The capture antibody is mouse monoclonal antibody m5B7.7 as produced from a hybridoma deposited at the ATCC under Deposit No. PTA-121871 or an antigen-binding fragment, variant, or derivative thereof and the detection antibody is rat monoclonal antibody R11A2.15 as produced from a hybridoma deposited at the ATCC under Deposit No. PTA-121872 or an antigen-binding fragment, variant, or derivative thereof;

The capture antibody is mouse monoclonal antibody m5B7.7 as produced from a hybridoma deposited at the ATCC under Deposit No. PTA-121871 or an antigen-binding fragment, variant, or derivative thereof and the detection antibody is rat monoclonal antibody R11A9.11 as produced from a hybridoma deposited at the ATCC under Deposit No. PTA-121873 or an antigen-binding fragment, variant, or derivative thereof;

The capture antibody is rat monoclonal antibody R11A2.15 as produced from a hybridoma deposited at the ATCC under Deposit No. PTA-121872 or an antigen-binding fragment, variant, or derivative thereof and the detection antibody is mouse monoclonal antibody m3B7.6 as produced from a hybridoma deposited at the ATCC under Deposit No. PTA-121870 or an antigen-binding fragment, variant, or derivative thereof;

The capture antibody is rat monoclonal antibody R11A2.15 as produced from a hybridoma deposited at the ATCC under Deposit No. PTA-121872 or an antigen-binding fragment, variant, or derivative thereof and the detection antibody is mouse monoclonal antibody m5B7.7 as produced from a hybridoma deposited at the ATCC under Deposit No. PTA-121871 or an antigen-binding fragment, variant, or derivative thereof;

The capture antibody is rat monoclonal antibody R11A9.11 as produced from a hybridoma deposited at the ATCC under Deposit No. PTA-121873 or an antigen-binding fragment, variant, or derivative thereof and the detection antibody is mouse monoclonal antibody m3B7.6 as produced from a hybridoma deposited at the ATCC under Deposit No. PTA-121870, or an antigen-binding fragment, variant, or derivative thereof; and/or The capture antibody is rat monoclonal antibody R11A9.11 as produced from a hybridoma deposited at the ATCC under Deposit No. PTA-121873 or an antigen-binding fragment, variant, or derivative thereof and the detection antibody is mouse monoclonal antibody m5B7.7 as produced from a hybridoma deposited at the ATCC under Deposit No. PTA-121871 or an antigen-binding fragment, variant, or derivative thereof.

In certain aspects, the disclosure provides a method of measuring the amount of DPP-4 in a sample obtained from a subject, where the method includes assaying the sample using the provided immunoassay or kit, and/or the provided antibody, or fragment, variant, or derivative thereof, or a combination of two or more such antibodies (including, e.g., antibodies m3B7.6, m5B7.7, R11A2.15, and/or R11A9.11). In certain aspects, the sample can be one or more of whole blood, serum, plasma, saliva, urine, sputum, bronchoalveolar lavage fluid, lung epithelial cells, or nasal polyps, or skin. In certain aspects, the subject has a disease or condition selected from the group consisting of: an IL-13-mediated disease or disorder, a pulmonary disease or disorder, and a chronic inflammatory skin disease or disorder. For example, the disease or condition can be asthma, atopic asthma, corticosteroid naive asthma, chronic asthma, corticosteroid resistant asthma, corticosteroid refractory asthma, asthma due to smoking, asthma uncontrolled on corticosteroids, idiopathic pulmonary fibrosis (IPF), chronic obstructive pulmonary disease (COPD), ulcerative colitis (UC), atopic dermatitis (AD), allergic rhinitis, chronic rhinosinusitis, skin fibrosis, allergic contact dermatitis, eczema and/or psoriasis. In certain aspects, the sample can be obtained from the subject and can be submitted for measurement of the DPP-4 level in the sample. In certain aspects, the subject can be an asthma patient, and the sample taken from the patient can be serum.

BRIEF DESCRIPTION OF THE DRAWINGS/FIGURES

FIG. 1: Draining lymph node injection sites for RIMMS protocol. Mouse and rat monoclonal antibodies specific for human DPP-4 were produced using the Repetitive Immunization at Multiple Sites (RIMMS) protocol (Kilpatrick, K., et al., Hybridoma 16:381-389 (2009)). Briefly, two Wistar rats were immunized with 30, 15, 7, 3, 3, and 3 µg CD26 on days 0, 2, 5, 7, 9, and 13, respectively, into draining lymph node sites A, B, and C as shown in FIG. 1. Mouse immunization followed the same schedule but with half the amount of antigen at each time point.

FIGS. 2A-D: Anti-DPP-4 mouse and rat antibodies are specific for human DPP-4 as shown using a direct binding ELISA. Direct binding ELISA against human DPP-4 (r-DPP-4-his) (A) or human gp130-his (B) using pre-immune (left side) or day 13 test-bleed (right side) sera from two rats (R9472 and R9473) immunized with human DPP-4. Day 13 rat sera specifically binds to human DPP4, while no specific binding is seen using pre-immune sera. Direct binding ELISA against human DPP-4 (r-DPP-4-his) (C) or human gp130-his (D) using pre-immune (left side) and 13 day test-bleed (right side) sera from five mice (ms9447, ms9448, ms9449, ms9450 and ms9451) immunized with human DPP-4-. Day 13 mouse sera specifically binds to human DPP-4, while no specific binding is seen using pre-immune sera.

Figure 3A:
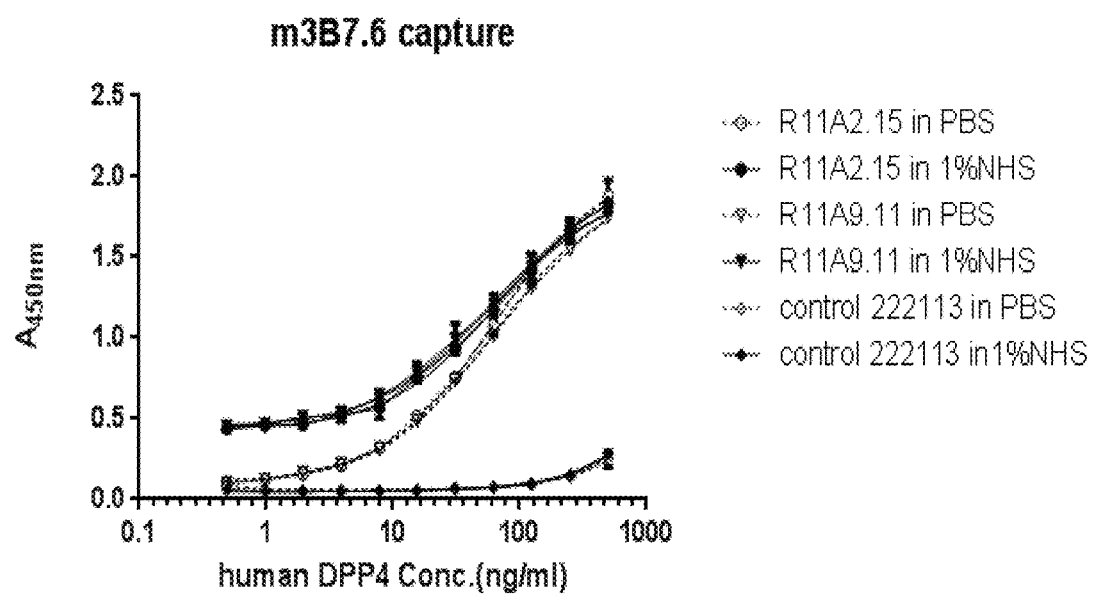
Figure 3B:
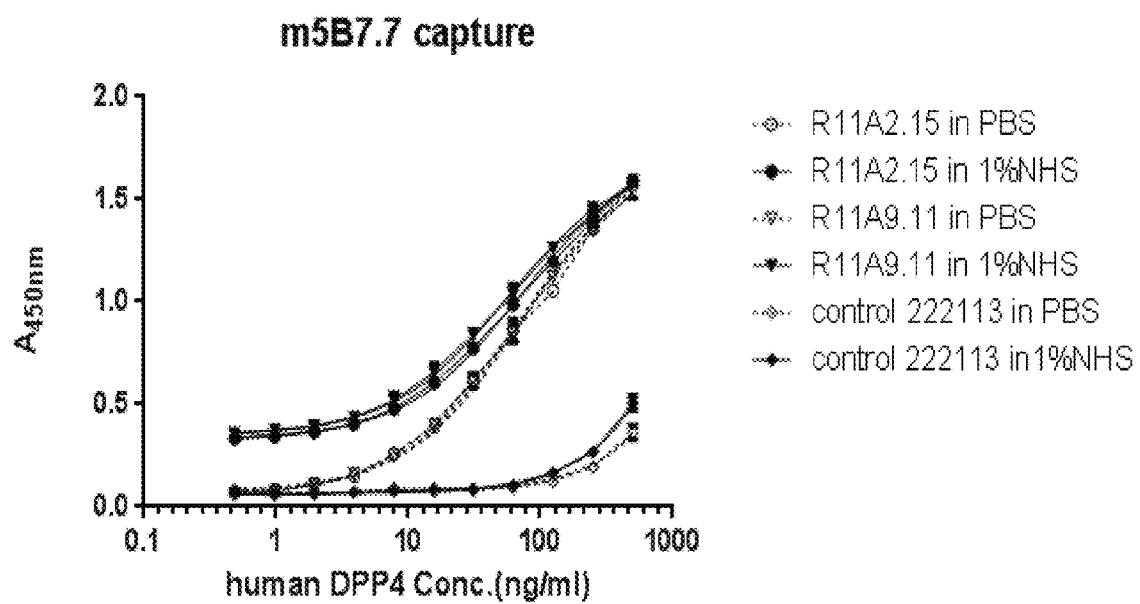

FIGS. 3A-B: Detection of human DPP-4 using m3B7.6 antibody (A) or m5B7.7 (B) as the capture antibody in an immunoassay. A. DPP-4 was added to PBS or in 1% normal human serum (NHS) using m3B7.6 as the capture antibody and R11A2.15, R11A9.11, or control antibody R222113 (R&D Systems Catalog No. MAB1180) as the detection antibody, in a sandwich ELISA assay. m3B7.6+R11A2.15 or m3B7.6+R11A9.11 provided the best sensitivity in measuring human DPP-4 in a sandwich ELISA assay. B. DPP-4 was added to PBS or in 1% normal human serum (NHS) using m5B7.7 as the capture antibody and R11A2.15, R11A9.11, or control antibody R222113 (R&D Systems Catalog No. MAB1180) as the detection antibody, in a sandwich ELISA assay. m5B7.7+R11A2.15 or m5B7.7+R11A9.11 provided the best sensitivity in measuring human DPP-4 in a sandwich ELISA assay. These results, in combination with the results reported in FIG. 2, demonstrate that antibodies m3B7.6, m5B7.7, R11A2.15, and R11A9.11 detect both endogenous and recombinant human DPP4. In addition, the commercially available antibody (R222113) failed to detect DPP4 in these immunoassays, compared to antibodies m3B7.6, m5B7.7, R11A2.15, and R11A9.11 which detected DPP-4.

FIGS. 4A-E: Mouse monoclonal antibodies m3B7.6 and m5B7.7 compete with each other, while the rat monoclonal antibodies R11A2.15 and R11A9.11 compete with each other. A. Schematic of the OCTET assay used to determine relative binding specificities and competition profiles of m3B7.6, m5B7.7, R11A2.15, and R11A9.11 as shown in FIGS. 4B-E. Briefly, the testing antibody was first biotinylated and then captured on a streptavidin biosensor at concentration of 20 µg/ml in 200 µl for 5 min. The biosensor was then washed with 200 µL of PBS buffer for 1 min, and then incubated with recombinant human DPP-4 at 10 µg/mL for 5 min and was washed with 200 µL of PBS buffer for 1 min. The competitor antibodies were mixed with testing antibody in 1:1 ratio and at a final concentration of 20 µg/ml each and loaded onto the biosensor in 200 µl for 5 min. Competitor antibodies displaying additional bindings to the testing antibody were deemed to have different epitopes. Otherwise they were considered to share the same epitope. B. OCTET assay results using m3B7.6 (a) as the testing antibody. m5B7.7 (b) showed the same binding profile as m3B7.6 (a) while R11A2.15 (c) and R11A9.11 (d) showed different binding profiles than m3B7.6 (a). On the basis of these results, antibodies m3B7.6 and m5B7.7 share the same or overlapping epitope. C. OCTET assay results using m5B7.7 (b) as the testing antibody. m3B7.6 (a) showed the same binding profile as m5B7.7 (b), while R11A2.15 (c) and R11A9.11 (d) showed different binding profiles than m5B7.7 (b). On the basis of these results, antibodies m5B7.7 and m3B7.6 share the same or overlapping epitope. D. OCTET assay results using R11A2.15 (c) as the testing antibody. R11A9.11 (d) showed the same binding profile as R11A2.15 (c), while m3B7.6 (a) and m5B7.7 (b) showed different binding profiles than R11A2.15 (c). On the basis of these results, antibodies R11A2.15 and R11A9.11 share the same or overlapping epitope E. OCTET assay results using R11A9.11 (d) as the testing antibody., R11A2.15(c) showed the same binding profile as R11A9.11 (d), while m3B7.6 (a) and m5B7.7 (b) showed different binding profiles than R11A9.11 (d). On the basis of these results, antibodies R11A9.11 and R11A2.15 share the same or overlapping epitope.

DETAILED DESCRIPTION

The present disclosure provides anti-DPP-4 monoclonal antibodies, assay kits comprising one or more of these antibodies, and robust, sensitive, and specific immunoassays using one or more of these antibodies for the detection and measurement of DPP-4 levels in samples obtained from human patients.

In this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Wherever aspects are described herein with the language "comprising," otherwise analogous aspects described in terms of "consisting of" and/or "consisting essentially of" are also provided.

The term "about" as used in connection with a numerical value throughout the specification and the claims denotes an interval of accuracy, familiar and acceptable to a person skilled in the art. In general, such interval of accuracy is ±10%.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

An "isolated" substance, composition, entity, and/or any combination of substances, compositions, or entities, or any grammatical variants thereof, e.g., isolated biological material, is a substance that is not in its natural milieu. No particular level of purification is required. For example, an isolated antibody is an antibody that is not produced or situated in its native or natural environment. Recombinantly produced biological materials are considered isolated as disclosed herein, as are materials that are produced in a non-native cell, such as a hybridoma. A substance, e.g., biological material, is also considered "isolated" if it has been separated, fractionated, or partially or substantially purified by any suitable technique. In certain aspects, an isolated substance, e.g., isolated biological material, can be "non-naturally occurring."

As used herein, the term "non-naturally occurring" substance, composition, entity, and/or any combination of substances, compositions, or entities, or any grammatical variants thereof, is a conditional term that explicitly excludes, but only excludes, those forms of the substance, composition, entity, and/or any combination of substances, compositions, or entities that are well-understood by persons of ordinary skill in the art as being "naturally-occurring," or that are, or might be at any time, determined or interpreted by a judge or an administrative agency such as the United States Patent and Trademark Office, or judicial body to be, "naturally-occurring." For example, the term "a non-naturally occurring antibody explicitly excludes those antibodies that exist in nature, e.g., an antibody that would naturally be present in the immune system of a mouse exposed to a normal milieu of antigenic stimulus, or an antibody finally determined by an administrative body, e.g., the United States Patent and Trademark Office, or a judicial body, e.g., a federal court, to be "naturally-occurring."

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

The term "expression" as used herein refers to a process by which a gene produces a biochemical, for example, transporter molecule provided herein. The process includes any manifestation of the functional presence of the gene within the cell including, without limitation, gene knockdown as well as both transient expression and stable expression. It includes without limitation transcription of the gene into one or more mRNAs, and the translation of such mRNAs into one or more polypeptides. If the final product is a biochemical, expression includes the creation of that biochemical and any precursors.

An "expression product" can be either a nucleic acid, e.g., a messenger RNA produced by transcription of a gene, or a polypeptide. Expression products described herein further include nucleic acids with post transcriptional modifications, e.g., polyadenylation, or polypeptides with post translational modifications, e.g., methylation, glycosylation, the addition of lipids, association with other protein subunits, proteolytic cleavage, and the like.

The term "vector" or "expression vector" is used herein to mean vectors used as a vehicle for introducing into and expressing an expression product of interest in a host cell. As known to those skilled in the art, such vectors can easily be selected from the group consisting of plasmids, phages, viruses and retroviruses. In general, vectors can comprise a selection marker, appropriate restriction sites to facilitate cloning of a particular nucleic acid and the ability to enter and/or replicate in eukaryotic or prokaryotic cells. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The term "host cell" refers to a cell that harbors a vector constructed using recombinant DNA techniques and encoding at least one expression product. In descriptions of processes for the isolation of an expression product from recombinant hosts, the terms "cell" and "cell culture" are used interchangeably to denote the source of the expression product unless it is clearly specified otherwise, i.e., recovery of the expression product from the "cells" means either recovery from spun down whole cells, or recovery from the cell culture containing both the medium and the suspended cells.

The terms "polypeptide," "peptide," and "protein" are used interchangeably herein to refer to polymers of amino acids of any length. The polymer can be linear or branched, it can comprise modified amino acids, and non-amino acids can interrupt it. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this disclosure are based upon antibodies, in certain embodiments, the polypeptides can occur as single chains or associated chains.

The term "DPP-4" as used herein refers to the dipeptidyl peptidase IV protein (EC 3.4.14.5; Uniprot: P27487 (membrane bound form: SEQ ID NO: 5; soluble form SEQ ID NO: 6) encoded by the DPP-4 gene (cDNA: SEQ ID NO: 7). DPP-4 is also known as DPP-IV, adenosine deaminase complexing protein 2, or CD26 (cluster of differentiation 26). DPP-4 is related to attractin, FAP, DPP8 and DPP9. DPP-4 is a highly conserved multifunctional type II transmembrane glycoprotein, which is present both in circulation (plasma) and on the surface of several cell types, including epithelial, endothelial and lymphoid cells. DPP-4 is part of the serine protease family that is involved in T-cell costimulation, chemokine biology, type II diabetes, and tumor biology (Zhong et al., Atherosclerosis 2013; 226:305-314). The endogenous substrates of DPP-4 include a wide variety of proline-containing peptides such as growth factors, chemokines, neuropeptides and vasoactive peptides (Gorrell, M., Clin. Sci. 108, 277-292, 2005; McIntosh, C. H. S., et al. Int. J. Biochem. Cell Biol. 38, 860-872, 2006). A role for DPP-4 in inflammatory respiratory diseases like asthma is suggested by Giovannini-Chami (Giovannini-Chami et al., European Respiratory Journal. 2012 May; 39(5):1197-205), who found elevated DPP-4 transcripts (and other Th2 signature genes) in the nasal epithelia of children with dust mite allergic rhinitis, associated with uncontrolled asthma. The term DPP-4 also includes fragments, variants (e.g., the K1R, V7I, S437I, T557I, D663E variants known in the arts), and derivatives thereof (e.g., glycosylated or aglycosylated protein forms of the DPP-4 protein, or otherwise chemically modified forms of the protein).

The term "level" or "amount", e.g., as in "DPP-4 level" or "amount of DPP-4" refers to a measurement that is made using an analytical method for detecting presence or expression of DPP-4 (protein expression) in a biological sample and that indicates the presence, absence, absolute amount or concentration, relative amount or concentration, titer, expression level, ratio of measured levels, or the like, of, for, or corresponding to DPP-4 in the biological sample. The exact nature of the "value" or "level" depends on the specific designs and components of the particular analytical method employed to detect DPP-4 (e.g., immunoassays as provided herein). See, e.g., U.S. 2010/00221752.

As used herein with reference to DPP-4, the terms "elevated DPP-4," "high DPP-4," "elevated DPP-4 level," or "high DPP-4 level" refer to a level in a biological sample (e.g., blood serum) that is higher than a normal level or range. The normal level or range for DPP-4 is defined in accordance with standard practice. Thus, the level measured in a particular biological sample can be compared with level or range of levels determined in similar normal samples. The level of DPP-4 is said to be elevated where the DPP-4 is present in the test sample at a higher level or range than in a normal sample.

As used herein, the term "antibody" (or a fragment, variant, or derivative thereof) refers to at least the minimal portion of an antibody which is capable of binding to antigen, e.g., at least the variable domain of a heavy chain (VH) and the variable domain of a light chain (VL) in the context of a typical antibody produced by a B cell. Basic antibody structures in vertebrate systems are relatively well understood. See, e.g., Harlow et al., Antibodies: A Laboratory Manual, (Cold Spring Harbor Laboratory Press, 2nd ed. 1988). Unless otherwise noted, an antibody "fragment," "variant," or "derivative" refers to an antigen-binding "fragment," "variant," or "derivative."

The terms "fragment," "variant," "derivative" and "analog" when referring to an antibody as disclosed herein can include any antibody that retains at least some of the activity, e.g., antigen-binding activity, of the reference antibody, but which is structurally different. Fragments of antibodies include, for example, e.g., Fab, Fab' and F(ab')2, Fd, Fvs, single-chain Fvs (scFv), single-chain antibodies, disulfide-linked Fvs (sdFv), fragments. Variants include fragments as described above, and also antibodies with altered amino acid sequences, e.g., in the variable domains, due to amino acid substitutions, deletions, or insertions. Variants can occur spontaneously or be intentionally constructed. Intentionally constructed variants can be produced using art-known mutagenesis techniques. Variant antibodies can comprise conservative or non-conservative amino acid substitutions, deletions or additions. The variations are limited only by the constraint that the antibody maintain a function of the reference antibody, e.g., binding to the same epitope as the reference antibody, or competitively inhibiting the reference antibody. Derivatives are antibodies that have been altered so as to exhibit additional features not found on the native antibody. Examples include fusion proteins comprising an antigen-binding domain of the antibody, or conjugated antibodies. A "derivative" antibody can also comprise one or more amino acids chemically derivatized by reaction of a functional side group. Also included as "derivatives" are those antibodies that contain one or more standard or synthetic amino acid derivatives of the twenty standard amino acids. For example, 4-hydroxyproline can be substituted for proline; 5-hydroxylysine can be substituted for lysine; 3-methylhistidine can be substituted for histidine; homoserine can be substituted for serine; and ornithine can be substituted for lysine.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like.

As indicated above, the variable region allows the binding molecule to selectively recognize and specifically bind epitopes on antigens. That is, the VL domain and VH domain, or a subset of the complementarity determining regions (CDRs), of an antibody combine to form the variable region that defines a three-dimensional antigen-binding site. This quaternary binding molecule structure forms the antigen-binding site present at the end of each arm of the Y. More specifically, the antigen-binding site is defined by three CDRs on each of the VH and VL chains.

In antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Human Services, (1983); and Chothia and Lesk, J. Mol. Biol., 196:901-917 (1987), which are incorporated herein by reference in their entireties).

In the cases where there are two or more definitions of a term that is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., J. Mol. Biol. 196: 901-917 (1987), which are incorporated herein by reference, where the definitions include overlapping or subsets of amino acid residues when compared against each other. Nevertheless, application of either definition to refer to a CDR of an antibody or variants thereof is intended to be within the scope of the term as defined and used herein.

Antibodies or antigen-binding fragments, variants, or derivatives thereof include, but are not limited to, polyclonal, monoclonal, human, humanized, or chimeric antibodies, single chain antibodies, epitope-binding fragments, e.g., Fab, Fab' and F(ab')2, Fd, Fvs, single-chain Fvs (scFv), single-chain antibodies, disulfide-linked Fvs (sdFv), fragments comprising either a VL or VH domain, fragments produced by a Fab expression library. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds," it is generally meant that an antibody or fragment, variant, or derivative thereof binds to an epitope via its antigen-binding domain, and that the binding entails some complementarity between the antigen-binding domain and the epitope. According to this definition, an antibody is said to "specifically bind" to an epitope when it binds to that epitope via its antigen-binding domain more readily than it would bind to a random, unrelated epitope.

An antibody or fragment, variant, or derivative thereof is said to competitively inhibit binding of a reference antibody or antigen-binding fragment to a given epitope if it preferentially binds to that epitope to the extent that it blocks, to some degree, binding of the reference antibody or antigen-binding fragment to the epitope. Competitive inhibition can be determined by any method known in the art, for example, competition ELISA assays. A binding molecule can be said to competitively inhibit binding of the reference antibody or antigen-binding fragment to a given epitope by at least 90%, at least 80%, at least 70%, at least 60%, or at least 50%.

Antibodies or antigen-binding fragments, variants, or derivatives thereof disclosed herein can be described or specified in terms of the epitope(s) or portion(s) of an antigen, e.g., a target polysaccharide that they recognize or specifically bind. For example, the portion of human DPP-4 that specifically interacts with the antigen-binding domain of an antibody provided in this disclosure is an "epitope."

As used herein, the term "IL-13-mediated disease or disorder" refers to any pathology caused by (alone or in association with other mediators), exacerbated by, associated with, or prolonged by abnormal levels of IL-13 in the subject having the disorder. Non-limiting examples of IL-13-mediated diseases or disorders include asthma, idiopathic pulmonary fibrosis (IPF), chronic obstructive pulmonary disease (COPD), ulcerative colitis (UC), atopic dermatitis (AD), allergic rhinitis, or chronic rhinosinusitis.

As used herein, the term "pulmonary disease or disorder" refers to any pathology affecting at least in part the lungs or respiratory system. Non-limiting examples include asthma, atopic asthma, corticosteroid naive asthma, chronic asthma, corticosteroid resistant asthma, corticosteroid refractory asthma, asthma due to smoking, asthma uncontrolled on corticosteroids, IPF, COPD, allergic rhinitis, or chronic rhinosinusitis. In certain aspects, the pulmonary disease or disorder is IL-13-mediated.

As used herein, the term "chronic inflammatory skin disease or disorder" refers to any pathology affecting at least in part the skin. Non-limiting examples include atopic dermatitis, skin fibrosis, allergic contact dermatitis, eczema or psoriasis. In certain aspects, the chronic inflammatory skin disease or disorder is IL-13-mediated.

The term "asthma" refers to diseases that present as reversible airflow obstruction and/or bronchial hyper-responsiveness in some instances is associated with underlying inflammation. Examples of asthma include allergic asthma, atopic asthma, corticosteroid naive asthma, chronic asthma, corticosteroid resistant asthma, corticosteroid refractory asthma, asthma due to smoking, asthma uncontrolled on corticosteroids and other asthmas as mentioned, e.g., in the Expert Panel Report 3: Guidelines for the Diagnosis and Management of Asthma, National Asthma Education and Prevention Program (2007) ("NAEPP Guidelines"), incorporated herein by reference in its entirety.

The term "COPD" as used herein refers to chronic obstructive pulmonary disease. The term "COPD" includes two main conditions: emphysema and chronic obstructive bronchitis.

The term "Idiopathic Pulmonary Fibrosis" (IPF) refers to a disease characterized by progressive scarring, or fibrosis, of the lungs. It is a specific type of interstitial lung disease in which the alveoli gradually become replaced by fibrotic tissue. With IPF, progressive scarring causes the normally thin and pliable tissue to thicken and become stiff, making it more difficult for the lungs to expand, preventing oxygen from readily getting into the bloodstream. See, e.g., Am. J. Respir. Crit. Care Med. 2000. 161:646-664.

The term "Ulcerative colitis" (UC) refers to an inflammatory disorder of the gastrointestinal (GI) tract that affects the colorectum which includes characteristic ulcers, or open sores. UC is an intermittent disease, with periods of exacerbated symptoms, and periods that are relatively symptom-free. Symptom of active disease include constant diarrhea mixed with blood that persists for an extended period (weeks), weight loss, chronic loss of blood from the GI tract, anemia, abdominal pain, and mild discomfort to painful bowel movements or painful abdominal cramping with bowel movements. See, e.g., Danese, et al. N Engl J Med. 2011 365(18):1713-25.

As used herein, the term "atopic dermatitis" refers to a chronic inflammatory, relapsing, non-contagious and itchy skin disorder that is often associated with other atopic disorders such as allergic rhinitis and asthma (Bieber, New England Journal of Medicine, 2008, 358: 1483-1494). The term "atopic dermatitis" is equivalent to "neurodermatitis", "atopic eczema" or "endogenous eczema". Particular forms of atopic dermatitis, which get their names from the place where they occur or from their appearance or from the stress factors which provoke them, are, according to the present disclosure also comprised by the term "atopic dermatitis". These include, but are not limited to, eczema flexurarum, eczema mulluscatum, eczema verrucatum, eczema vaccinatum, eczema dyskoides, dyshydrotic eczema, microbial eczema, nummular eczema, seborrhobic eczema and other forms of eczema; perioral dermatitis and periorbital dermatitis. As used herein, the term atopic dermatitis also comprises the frequently occurring bacterial secondary infections such as those due to e.g. *Staphylococcus aureus* infections, pyodermas such as impetigo contagiosa and its derivatives as well as the follicularis barbae or viral secondary infections. IL-13 is involved in the pathogenesis of the disease and is an important in vivo inducer. See, e.g., Oh et al., J. Immunol. 186:7232-42 (2011); Tazawa et al., Arch. Dermatol. Res. 295:459-464 (2004); Metwally et al. Egypt J. Immunol. 11:171-7 (2004).

The terms "subject" or "patient" as used herein refer to any subject, particularly a mammalian subject, including any human or nonhuman animal. The term "nonhuman animal" includes all vertebrates, e.g., mammals and non-mammals, such as nonhuman primates, sheep, dogs, cats, horses, cows, bears, chickens, amphibians, reptiles, etc.

In some aspects of the present disclosure, a subject is a naïve subject. A naïve subject is a subject that has not been administered a therapy, for example a therapeutic agent. In some aspects, a naïve subject has not been treated with a therapeutic agent prior to being diagnosed as having an IL-13-mediated disease or disorder, for example, asthma, IFP, COPD, AD, or UC. In another aspect, a subject has received therapy and/or one or more doses of a therapeutic agent (e.g., a therapeutic agent capable of modulating an inflammatory response associated with an IL-13-mediated disease or disorder, a pulmonary disease or disorder, a chronic inflammatory skin disease or disorder or an inflammatory bowel disease or disorder) prior to being diagnosed as having an IL-13-mediated disease or disorder.

As used herein, the term "IL-13 antagonist" refers to any agent, which can affect the expression, activity, or half-life of IL-13 either in vitro or in vivo, or symptoms, pathology, or sequelae caused by or exacerbated by IL-13 in a subject with an IL-13-mediated disease or disorder. An IL-13 antagonist can be any "therapeutic agent" as defined below, which either directly or indirectly can inhibit, lessen, or neutralize IL-13 activity, inhibit or reduce IL-13 expression, reduce IL-13 half-life, or can prevent exacerbation of symptoms due to IL-13. In certain aspects, an IL-13 antagonist is an anti-IL-13 monoclonal antibody, e.g., tralokinumab (SEQ ID NOs 3 and 4), or other anti-IL-13 monoclonal antibodies described in U.S. Pat. Appl. Publ. No. 2012-0052060, published Mar. 1, 2012, herein incorporated by reference in its entirety. In other aspects, the IL-13 antagonists include, without limitation: (a) an anti-human-IL-13 antibody, for example, Lebrikizumab (SEQ ID NOs 1 and 2) (MILR1444A/RG3637, Roche/Genentech), ABT-308 (Abbott), GSK679586 (GlaxoSmithKline) or QAX576 (Novartis); (b) an anti-human-IL-13Rα1 antibody, for example, Merck MK6105; (c) an IL-13-toxin conjugate such as IL-13-PE38QQR (NeoPharm, Inc.); (d) an IL-4 mutein Aerovant™ (Aerovance, Inc.); (e) an anti-IL-4Rα antibody such as dupilumab/REGN668 (Regeneron); (f) a double-stranded oligonucleotide directed against IL-4Rα such as AIR645 (Isis); or (g) an IL-4/IL-13 bispecific antibody such as GSK2434735 (Glaxo SmithKline).

The term "therapeutic agent" as used herein refers to any therapeutically active substance that is administered to a subject to produce a desired, usually beneficial, effect. The term therapeutic agent includes, e.g., classical low molecular weight therapeutic agents commonly referred to as small molecule drugs and biologics including but not limited to: antibodies or active fragments thereof, peptides, lipids, protein drugs, protein conjugate drugs, enzymes, oligonucleotides, ribozymes, genetic material, prions, virus, bacteria, and eukaryotic cells. A therapeutic agent can also be a pro-drug, which metabolizes into the desired therapeutically active substance when administered to a subject. In some aspects, the therapeutic agent is a prophylactic agent. In addition, a therapeutic agent can be pharmaceutically formulated. A therapeutic agent can also be a radioactive isotope or agent activated by some other form of energy such as light or ultrasonic energy, or by other circulating molecules that can be systemically administered.

The term "sample" as used herein includes any biological fluid or issue, such as whole blood, serum, muscle, saliva obtained from a subject. Samples include any biological fluid or tissue, such as whole blood, serum, muscle, saliva, urine, synovial fluid, bone marrow, cerebrospinal fluid, nasal secretions, sputum, amniotic fluid, bronchoalveolar lavage fluid, lung tissue, peripheral blood mononuclear cells, total white blood cells, lymph node cells, spleen cells, tonsil cells, or skin. In some specific aspects, that sample is blood or a fraction thereof, muscle, skin, or a combination thereof. Samples can be obtained by any means known in the art.

In order to apply the methods and systems of the disclosure, samples from a patient can be obtained at any time. In some cases, successive samples can be obtained from the patient after therapy has commenced or after therapy has ceased. Samples can, for example, be requested by a healthcare provider (e.g., a doctor) or healthcare benefits provider, obtained and/or processed by the same or a different healthcare provider (e.g., a nurse, a hospital) or a clinical laboratory, and after processing, the results can be forwarded to yet another healthcare provider, healthcare benefits provider or the patient. Similarly, the measuring/determination of one or more scores, comparisons between scores, evaluation of the scores and treatment decisions can be performed by one or more healthcare providers, healthcare benefits providers, and/or clinical laboratories.

As used herein, the term "healthcare provider" refers to individuals or institutions that directly interact and administer to living subjects, e.g., human patients. Non-limiting examples of healthcare providers include doctors, nurses, technicians, therapist, pharmacists, counselors, alternative medicine practitioners, medical facilities, doctor's offices, hospitals, emergency rooms, clinics, urgent care centers, alternative medicine clinics/facilities, and any other entity providing general and/or specialized treatment, assessment, maintenance, therapy, medication, and/or advice relating to all, or any portion of, a patient's state of health, including but not limited to general medical, specialized medical, surgical, and/or any other type of treatment, assessment, maintenance, therapy, medication and/or advice.

As used herein, the term "clinical laboratory" refers to a facility for the examination or processing of materials derived from a living subject, e.g., a human being. Non-limiting examples of processing include biological, biochemical, serological, chemical, immunohematological, hematological, biophysical, cytological, pathological, genetic, or other examination of materials derived from the human body for the purpose of providing information, e.g., for the diagnosis, prevention, or treatment of any disease or impairment of, or the assessment of the health of living subjects, e.g., human beings. These examinations can also include procedures to collect or otherwise obtain a sample, prepare, determine, measure, or otherwise describe the presence or absence of various substances in the body of a living subject, e.g., a human being, or a sample obtained from the body of a living subject, e.g., a human being.

As used herein, the term "healthcare benefits provider" encompasses individual parties, organizations, or groups providing, presenting, offering, paying for in whole or in part, or being otherwise associated with giving a patient access to one or more healthcare benefits, benefit plans, health insurance, and/or healthcare expense account programs.

In some aspects, a healthcare provider can administer or instruct another healthcare provider to administer or use any of the immunoassays or kits disclosed herein to measure DPP-4. A healthcare provider can implement or instruct another healthcare provider or patient to perform the following actions: obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, administer a therapy (e.g., a therapeutic agent that treats an IL-13-mediated disease or disorder such as asthma, IPF, COPD, AD, or UC), commence the administration of a therapy, cease the administration of a therapy, continue the administration of a therapy, temporarily interrupt the administration of a therapy, increase the amount of an administered therapeutic agent, decrease the amount of an administered therapeutic agent, continue the administration of an amount of a therapeutic agent, increase the frequency of administration of a therapeutic agent, decrease the frequency of administration of a therapeutic agent, maintain the same dosing frequency on a therapeutic agent, replace a therapy or therapeutic agent by at least another therapy or therapeutic agent, combine a therapy or therapeutic agent with at least another therapy or additional therapeutic agent.

In some aspects, a healthcare benefits provider can authorize or deny, for example, collection of a sample, processing of a sample, submission of a sample, receipt of a sample, transfer of a sample, analysis or measurement a sample, quantification a sample, provision of results obtained after analyzing/measuring/quantifying a sample, transfer of results obtained after analyzing/measuring/quantifying a sample, comparison/scoring of results obtained after analyzing/measuring/quantifying one or more samples, transfer of the comparison/score from one or more samples, administration of a therapy or therapeutic agent, commencement of the administration of a therapy or therapeutic agent, cessation of the administration of a therapy or therapeutic agent, continuation of the administration of a therapy or therapeutic agent, temporary interruption of the administration of a therapy or therapeutic agent, increase of the amount of administered therapeutic agent, decrease of the amount of administered therapeutic agent, continuation of the administration of an amount of a therapeutic agent, increase in the frequency of administration of a therapeutic agent, decrease in the frequency of administration of a therapeutic agent, maintain the same dosing frequency on a therapeutic agent, replace a therapy or therapeutic agent by at least another therapy or therapeutic agent, or combine a therapy or therapeutic agent with at least another therapy or additional therapeutic agent.

In addition a healthcare benefits provides can, e.g., authorize or deny the prescription of a therapy, authorize or deny coverage for therapy, authorize or deny reimbursement for the cost of therapy, determine or deny eligibility for therapy, etc.

In some aspects, a clinical laboratory can, for example, collect or obtain a sample, process a sample, submit a sample, receive a sample, transfer a sample, analyze or measure a sample, quantify a sample, provide the results obtained after analyzing/measuring/quantifying a sample, receive the results obtained after analyzing/measuring/quantifying a sample, compare/score the results obtained after analyzing/measuring/quantifying one or more samples, provide the comparison/score from one or more samples, obtain the comparison/score from one or more samples, or other related activities.

DPP-4 as a Biomarker

Elevated DPP-4 levels have been observed in asthma, COPD and AD patients (see, e.g., U.S. Provisional Application No. 61/931,878, filed Jan. 27, 2014; and U.S. Provisional Application No. 61/990,932, filed May 9, 2014, each incorporated herein by reference in its entirety). In addition, in a phase 2B clinical study of asthma patients, high serum DPP-4 levels predicted improved response rates in patients treated with an IL-13 antibody antagonist (tralokinumab) identifying DPP-4 as a predictive biomarker for IL-13-mediated disease or disorders including an IL-13-mediated pulmonary disease or disorder (e.g., asthma, IPF or COPD) or an IL-13-mediated chronic inflammatory skin disease or disorder (e.g., atopic dermatitis). See Brightling et al., Am J Respir Crit Care Med 189:A6670 (2014); and U.S. Provisional Application No. 61/931,878, filed Jan. 27, 2014; and U.S. Provisional Application No. 61/990,932, filed May 9, 2014, each incorporated herein by reference in its entirety.

Accordingly, an elevated DPP-4 level in patients with asthma, IPF, COPD, AD and UC, as well as other inflammatory diseases, pulmonary diseases or disorders, or chronic inflammatory skin diseases or disorders can be used to identify those patients who can benefit from particular therapies, including, but not limited to, therapies that neutralize IL-13 activity. Anti-DPP-4 antibodies and immunoassays and kits using the anti-DPP4 antibodies disclosed herein useful to measure DPP-4 levels in patients are provided.

Anti-DPP-4 Antibodies

This disclosure provides isolated anti-DPP-4 antibodies and antigen-binding fragments thereof. In certain aspects, the anti-DPP-4 antibodies and antigen-binding fragments provided herein can bind to human DPP-4.

The disclosure provides, in particular, two mouse monoclonal antibodies and two rat monoclonal antibodies that bind to human DPP-4. These antibodies were produced by standard hybridoma technology, and the hybridomas producing these antibodies have been deposited under the Budapest Treaty at the American Type Culture Collection, Manassas, Va. on Jan. 8, 2015. The mouse anti-DPP-4 antibodies are referred to herein as m3B7.6 and m5B7.7, and the rat anti-DPP-4 antibodies are referred to herein as R11A2.15, and R11A9.11. Also provided are antigen-binding fragments, variants, and/or derivatives of these antibodies. Also provided are antibodies that are related to these antibodies in that they bind to the same epitope, or they are capable of competitively inhibiting one or more of m3B7.6, m5B7.7, R11A2.15, and R11A9.11. Mouse monoclonal antibody m3B7.6 is produced from a hybridoma deposited at the American Type Culture Collection, Manassas, Va. (the ATCC) under Deposit No. PTA-121870, mouse monoclonal antibody m5B7.7 is produced from a hybridoma deposited at the ATCC under Deposit No PTA-121871, rat monoclonal antibody R11A2.15 is produced from a hybridoma deposited at the ATCC under Deposit No PTA-121872, and rat monoclonal antibody R11A9.11 is produced from a hybridoma deposited at the ATCC under Deposit No. PTA-121873.

In certain aspects, an isolated antibody or antigen-binding fragment, variant, or derivative thereof is provided, where the antibody binds to the same DPP-4 epitope as mouse monoclonal antibody m3B7.6 produced from a hybridoma deposited at the American Type Culture Collection (ATCC) under Deposit No. PTA-121870, mouse monoclonal antibody m5B7.7 produced from a hybridoma deposited at the ATCC under Deposit No. PTA-121871, rat monoclonal antibody R11A2.15 produced from a hybridoma deposited at the ATCC under Deposit No. PTA-121872, and/or rat monoclonal antibody R11A9.11 produced from a hybridoma deposited at the ATCC under Deposit No. PTA-121873.

In certain aspects, an isolated antibody or antigen-binding fragment, variant, or derivative thereof is provided, where the antibody competitively inhibits binding of mouse monoclonal antibody m3B7.6 produced from a hybridoma deposited at the American Type Culture Collection (ATCC) under Deposit No. PTA-121870, mouse monoclonal antibody m5B7.7 produced from a hybridoma deposited at the ATCC under Deposit No. PTA-121871, rat monoclonal antibody R11A2.15 produced from a hybridoma deposited at the ATCC under Deposit No. PTA-121872, and/or rat monoclonal antibody R11A9.11 produced from a hybridoma deposited at the ATCC under Deposit No. PTA-121873 to DPP-4, e.g., human DPP-4. For example, monoclonal antibodies m3B7.6 and m5B7.7 are capable of competitively inhibiting each other for binding to human DPP-4, and monoclonal antibodies R11A9.11 and R11A2.15 are capable of competitively inhibiting each other for binding to human DPP-4.

In certain aspects, an isolated anti-DPP-4 antibody or fragment, variant, or derivative thereof is provided, where the antibody comprises a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, where the CDRs of the isolated antibody, or fragment, variant, or derivative thereof are identical to the CDRs of mouse monoclonal antibody m3B7.6 produced from a hybridoma deposited at the American Type Culture Collection (ATCC) under Deposit No. PTA-121870, mouse monoclonal antibody m5B7.7 produced from a hybridoma deposited at the ATCC under Deposit No. PTA-121871, rat monoclonal antibody R11A2.15 produced from a hybridoma deposited at the ATCC under Deposit No. PTA-121872, and/or rat monoclonal antibody R11A9.11 produced from a hybridoma deposited at the ATCC under Deposit No. PTA-121873.

In certain aspects, an isolated anti-DPP-4 antibody or fragment, variant, or derivative thereof is provided, where the antibody comprises a VH and a VL identical to the VH and VL of mouse monoclonal antibody m3B7.6 produced from a hybridoma deposited at the American Type Culture Collection (ATCC) under Deposit No. PTA-121870, mouse monoclonal antibody m5B7.7 produced from a hybridoma deposited at the ATCC under Deposit No. PTA-121871, rat monoclonal antibody R11A2.15 produced from a hybridoma deposited at the ATCC under Deposit No. PTA-121872, and/or rat monoclonal antibody R11A9.11 produced from a hybridoma deposited at the ATCC under Deposit No. PTA-121873.

A person of ordinary skill in the art, upon obtaining one or more of the antibodies from one or more of the deposited hybridomas can isolate, clone, and sequence the expressed antibodies to determine the VH, VL, and CDR regions, without undue experimentation.

In certain aspects, a hybridoma is provided, where the hybridoma comprises the hybridoma deposited at the American Type Culture Collection (ATCC) under Deposit No. 121870, the hybridoma deposited at the ATCC under Deposit No. 121871, the hybridoma deposited at the ATCC under Deposit No. 121872, the hybridoma deposited at the ATCC under Deposit No. 121873, or a combination thereof.

In certain aspects, an antibody-producing cell culture is provided, where the cell culture can be used to express an anti-DPP-4 antibody or fragment, variant, or derivative thereof as provided herein. In certain aspects, the cell culture comprises a hybridoma deposited at the American Type Culture Collection (ATCC) under Deposit No. 121870, a hybridoma deposited at the ATCC under Deposit No. 121871, a hybridoma deposited at the ATCC under Deposit No. 121872, a hybridoma deposited at the ATCC under Deposit No. 121873, or a combination thereof.

Any anti-DPP-4 antibody or fragments, variants or derivatives thereof provided by this disclosure can further include additional polypeptides, e.g., a signal peptide to direct secretion. Additionally, anti-DPP-4 antibody or fragments, variants or derivatives thereof provided by this disclosure can be, for example, fusion polypeptides, Fab fragments, scFvs, or other derivatives, as described herein.

In certain aspects, an anti-DPP-4 antibody, or fragment, variant, or derivative thereof provided by this disclosure can be part of a fusion protein, that is, the antibody or antigen-binding fragment thereof can be fused to a heterologous polypeptide. The term "heterologous polypeptide" as used herein means that the polypeptide is derived from a distinct entity from the anti-DPP-4 antibody, or fragment, variant, or derivative thereof. In a non-limiting example, a "heterologous polypeptide" to be fused to an antibody or an antigen-binding fragment, variant, or derivative thereof can be derived from a non-immunoglobulin polypeptide of the same species, or an immunoglobulin or non-immunoglobulin heterologous polypeptide. In some aspects, the heterologous polypeptide can be, for example, a stabilizing polypeptide, a tag, a label, or a combination thereof.

In certain aspects, an anti-DPP-4 antibody or fragment, variant or derivative thereof provided by this disclosure can comprise a heterologous amino acid sequence or one or more other moieties not normally associated with an antibody (e.g., a peptide, a protein, an enzyme, a lipid, a heterologous antibody, or fragment, variant, or derivative thereof, a detectable label, polyethylene glycol (PEG), or a combination of two or more of any said agents). In further aspects, an anti-DPP-4 antibody or fragment, variant or derivative thereof provided by this disclosure can comprise a detectable label selected from the group consisting of an enzyme, a fluorescent label, a chemiluminescent label, a bioluminescent label, a radioactive label, or a combination of two or more of any said detectable labels. In certain aspects, the detectable label is biotin, which can interact with streptavidin conjugated, e.g., to an enzyme, e.g., horseradish peroxidase (HRP). In certain aspects, the detectable label is a ruthenium chelate, which can emit light upon exposure to electrical current. Other detectable labels are well-known to those of ordinary skill in the art.

Also provided herein is a composition comprising one or more of the anti-DPP-4 antibodies or fragments thereof as noted above. In certain aspects, a composition includes a "capture" antibody and a "detection" antibody, as described elsewhere herein. Compositions as provided herein can include without limitation buffers, carriers, and preservatives. Preservatives, stabilizers, buffers, antioxidants and/or other additives can include buffers such as phosphate, citrate, and other organic acids; antioxidants, such as ascorbic acid and methionine; preservatives such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol; low molecular weight polypeptides; proteins, such as serum albumin, gelatin, or immunoglobulins; hydrophilic polymers, such as polyvinylpyrrolidone; amino acids, such as glycine, glutamine, asparagine, histidine, arginine, or lysine; monosaccharides, disaccharides, and other carbohydrates including glucose, mannose, or dextrins; chelating agents, such as EDTA; sugars, such as sucrose, mannitol, trehalose, or sorbitol; salt-forming counter-ions, such as sodium; metal complexes (e.g. Zn-protein complexes); and/or non-ionic surfactants, such as TWEEN™, PLURONIC™, or polyethylene glycol (PEG). Compositions as provided herein can be mixed in a single vial or receptacle, or can be provided in two or more vials or receptacles, or as part of a kit, as described elsewhere herein.

Polynucleotides

This disclosure provides polynucleotides encoding any anti-DPP-4 antibody or a subunit (e.g., the heavy chain or the light chain), fragment, variant, or derivative thereof provided herein. In certain aspects an isolated polynucleotide or a polynucleotide composition comprising two or more polynucleotides is provided, which singly or collectively encodes an anti-DPP-4 antibody or a subunit (e.g., the heavy chain or the light chain), fragment, variant, or derivative thereof provided herein.

In certain aspects, this disclosure provides an isolated polynucleotide comprising a nucleic acid that encodes an anti-DPP-4 antibody or a subunit (e.g., the heavy chain or the light chain), fragment, variant, or derivative thereof, where the antibody comprises a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, where the CDRs of the isolated antibody, or fragment, variant, or derivative thereof are identical to the CDRs of mouse monoclonal antibody m3B7.6 produced from a hybridoma deposited at the American Type Culture Collection (ATCC) under Deposit No. PTA-121870, mouse monoclonal antibody m5B7.7 produced from a hybridoma deposited at the ATCC under Deposit No. PTA-121871, rat monoclonal antibody R11A2.15 produced from a hybridoma deposited at the ATCC under Deposit No. PTA-121872, and/or rat monoclonal antibody R11A9.11 produced from a hybridoma deposited at the ATCC under Deposit No. PTA-121873.

The disclosure also provides an isolated polynucleotide comprising a nucleic acid that encodes an anti-DPP-4 antibody or a subunit (e.g., the heavy chain or the light chain), fragment, variant, or derivative thereof, where the antibody comprises a VH and a VL identical to the VH and VL of mouse monoclonal antibody m3B7.6 produced from a hybridoma deposited at the American Type Culture Collection (ATCC) under Deposit No. PTA-121870, mouse monoclonal antibody m5B7.7 produced from a hybridoma deposited at the ATCC under Deposit No. PTA-121871, rat monoclonal antibody R11A2.15 produced from a hybridoma deposited at the ATCC under Deposit No. PTA-121872, and/or rat monoclonal antibody R11A9.11 produced from a hybridoma deposited at the ATCC under Deposit No. PTA-121873.

The disclosure further provides a composition comprising two or more polynucleotides that singly or collectively encodes an anti-DPP-4 antibody or a subunit (e.g., the heavy chain or the light chain), fragment, variant, or derivative thereof provided herein.

In certain aspects, a vector, or two or more vectors are provided, to facilitate display, screening, isolation, cloning, and/or expression of an anti-DPP-4 antibody or a subunit (e.g., the heavy chain or the light chain), fragment, variant, or derivative thereof provided herein. In certain aspects the vector or vectors is/are expression vectors.

In certain aspects, two or more nucleic acid molecules of a polynucleotide composition can be situated in the same vector. In certain aspects, the two or more nucleic acid molecules of the polynucleotide composition can be situated in at least two separate vectors.

Expression vectors are used express isolated polynucleotide(s) encoding an anti-DPP-4 antibody or a subunit (e.g., the heavy chain or the light chain), fragment, variant, or derivative thereof provided herein. Recombinant expression vectors are replicable DNA constructs which have synthetic or cDNA-derived DNA fragments encoding a polypeptide chain of a transporter molecule, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated.

In certain aspects an isolated polynucleotide or composition comprising two or more isolated polynucleotides is provided, comprising a nucleic acid molecule that is operably associated with a promoter, or the two or more nucleic acid molecules that are operably associated with two or more promoters, where the promoters can be the same or different.

Nucleic acid regions are "operably associated" when they are functionally related to each other. For example, DNA for a signal peptide (secretory leader) is operably associated with DNA for a polypeptide if it is expressed as a precursor which participates in the secretion of the polypeptide; a promoter is operably associated with a coding sequence if it controls the transcription of the sequence; or a ribosome binding site is operably associated with a coding sequence if it is positioned so as to permit translation.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR 1, pBR322, pMB9 and their derivatives, wider host range plasmids, such as M13 and filamentous single-stranded DNA phages.

In certain aspects an isolated host cell is provided that comprises a polynucleotide as provided herein. In certain aspects one or more isolated host cells are provided that comprise the two or more polynucleotides of the polynucleotide composition provided herein.

Suitable host cells for expression of transporter molecules provided herein include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems can also be employed to express an anti-DPP-4 antibody or a subunit (e.g., the heavy chain or the light chain), fragment, variant, or derivative thereof provided herein. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), NSO, HeLa and BHK cell lines. Mammalian expression vectors can comprise nontranscribed elements such as an origin of replication, a suitable promoter and enhancer operably associated with the gene to be expressed, and other 5' or 3' flanking nontranscribed sequences, and 5' or 3' nontranslated sequences, such as ribosome binding sites, a polyadenylation site, splice donor and acceptor sites, and transcriptional termination sequences. Baculovirus systems for production of heterologous proteins in insect cells are reviewed by Luckow and Summers, BioTechnology 6:47 (1988).

Host cells provided herein can be utilized in a method of making an anti-DPP-4 antibody or a subunit (e.g., the heavy chain or the light chain), fragment, variant, or derivative thereof provided herein, where the method includes (a) culturing the host cell and (b) isolating the antibody, fragment, or subunit expressed from the host cell.

Assays for Detecting DPP-4 Levels

This disclosure provides a method of measuring DPP-4 levels in a sample obtained from a subject comprising assaying the sample using an immunoassay employing at least one, e.g., at least two anti-DPP-4 antibodies or antigen-binding fragments thereof that recognize distinct epitopes on human DPP-4. Exemplary antibodies for use in this method include one or more of mouse monoclonal antibody m3B7.6 produced from a hybridoma deposited at the ATCC under Deposit No. PTA-121870, mouse monoclonal antibody m5B7.7 produced from a hybridoma deposited at the ATCC under Deposit No. PTA-121871, rat monoclonal antibody R11A2.15 produced from a hybridoma deposited at the ATCC under Deposit No. PTA-121872, and/or rat monoclonal antibody R11A9.11 produced from a hybridoma deposited at the ATCC under Deposit No. PTA-121873, and/or antigen-binding fragments, variants, or derivatives thereof, as described herein.

The method involves the use of a specific and sensitive immunoassay for the detection of DPP-4 in samples obtained from a subject. The samples are assayed in an immunoassay employing at least one, e.g., at least two anti-DPP-4 antibodies provided herein, e.g., mouse monoclonal antibody m3B7.6 produced from a hybridoma deposited at the ATCC under Deposit No. PTA-121870, mouse monoclonal antibody m5B7.7 produced from a hybridoma deposited at the ATCC under Deposit No. PTA-121871, rat monoclonal antibody R11A2.15 produced from a hybridoma deposited at the ATCC under Deposit No. PTA-121872, and/or rat monoclonal antibody R11A9.11 produced from a hybridoma deposited at the ATCC under Deposit No. PTA-121873, and/or antigen-binding fragments, variants, or derivatives thereof, as described herein.

For example, the disclosure provides a method of measuring DPP-4 levels in a sample obtained from a subject, comprising assaying the sample in an immunoassay employing at least one, e.g., at least two anti-DPP-4 antibodies or antigen-binding fragments, variants, or derivatives thereof that recognize distinct epitopes on human DPP-4. In one aspect, one of the at least two anti-DPP-4 antibodies comprises an isolated antibody or antigen-binding fragment, variant, or derivative thereof that binds to the same DPP-4 epitope as mouse monoclonal antibody m3B7.6 produced from a hybridoma deposited at the American Type Culture Collection (ATCC) under Deposit No. PTA-121870 or mouse monoclonal antibody m5B7.7 produced from a hybridoma deposited at the ATCC under Deposit No. PTA-121871, and one of the at least two anti-DPP-4 antibodies comprises an isolated antibody or antigen-binding fragment, variant, or derivative thereof that binds to the same DPP-4 epitope as rat monoclonal antibody R11A2.15 produced from a hybridoma deposited at the ATCC under Deposit No. PTA-121872, and/or rat monoclonal antibody R11A9.11 produced from a hybridoma deposited at the ATCC under Deposit No. PTA-121873.

In another aspect, one of the at least two anti-DPP-4 antibodies comprises an isolated antibody or antigen-binding fragment, variant, or derivative thereof that competitively inhibits binding of mouse monoclonal antibody m3B7.6 produced from a hybridoma deposited at the ATCC under Deposit No. PTA-121870, and/or mouse monoclonal antibody m5B7.7 produced from a hybridoma deposited at the ATCC under Deposit No. PTA-121871 to DPP-4; and one of the at least two anti-DPP-4 antibodies comprises an isolated antibody or antigen-binding fragment, variant, or derivative thereof that competitively inhibits binding of rat monoclonal antibody R11A2.15 produced from a hybridoma deposited at the ATCC under Deposit No. PTA-121872, and/or rat monoclonal antibody R11A9.11 produced from a hybridoma deposited at the ATCC under Deposit No. PTA-121873 to DPP-4.

In another aspect, one of the two or more anti-DPP-4 antibodies is an isolated antibody or antigen-binding fragment, variant, or derivative thereof comprising a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, wherein the CDRs of the isolated antibody, or fragment, variant, or derivative thereof are identical to the CDRs of mouse monoclonal antibody m3B7.6 produced from a hybridoma deposited at the ATCC under Deposit No. PTA-121870, and/or mouse monoclonal antibody m5B7.7 produced from a hybridoma deposited at the ATCC under Deposit No. PTA-121871; and one of the two or more anti-DPP-4 antibodies is an isolated antibody or antigen-binding fragment, variant, or derivative thereof comprising a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, wherein the CDRs of the isolated antibody, or fragment, variant, or derivative thereof are identical to the CDRs of rat monoclonal antibody R11A2.15 produced from a hybridoma deposited at the ATCC under Deposit No. PTA-121872, and/or rat monoclonal antibody R11A9.11 produced from a hybridoma deposited at the ATCC under Deposit No. PTA-121873.

In another aspect, one of the two or more anti-DPP-4 antibodies is an isolated antibody or antigen-binding fragment, variant, or derivative thereof comprising a VH and a VL identical to the VH and VL of mouse monoclonal antibody m3B7.6 produced from a hybridoma deposited at the ATCC under Deposit No. PTA-121870, and/or mouse monoclonal antibody m5B7.7 produced from a hybridoma deposited at the ATCC under Deposit No. PTA-121871; and one of the two or more anti-DPP-4 antibodies is an isolated antibody or antigen-binding fragment, variant, or derivative thereof comprising a VH and a VL identical to the VH and VL of rat monoclonal antibody R11A2.15 produced from a hybridoma deposited at the ATCC under Deposit No. PTA-121872, and/or rat monoclonal antibody R11A9.11 produced from a hybridoma deposited at the ATCC under Deposit No. PTA-121873.

Any of these antibodies or fragments thereof can be fused to one or more heterologous polypeptides, e.g., a stabilizing polypeptide, a tag, a label, or a combination thereof, or can be conjugated to a heterologous moiety, e.g., a peptide, a protein, an enzyme, a lipid, a heterologous antibody or fragment thereof, a detectable label, polyethylene glycol (PEG), or a combination of two or more of any the agents. In certain aspects, the antibody comprises a detectable label such as biotin or a ruthenium chelate. Other detectable labels are well known to those of ordinary skill in the art and are included in this disclosure.

In certain aspects, the immunoassay comprises a sandwich immunoassay, e.g., an enzyme-linked immunosorbent assay (ELISA) or a sandwich electrochemiluminescent (ECL) assay, in which a first anti-DPP-4 "capture" antibody or antigen-binding fragment thereof is attached to a solid support, antigen from a sample or standard is allowed to bind to the capture antibody, and then a second anti-DPP-4 "detection" antibody or antigen-binding fragment thereof is added, and detected either by an enzymatic reaction, an electrochemiluminescent reaction, radioactivity, or other detection method.

In certain aspects, the immunoassay comprises the following: first, the capture antibody, or fragment, variant, or derivative thereof is allowed to bind to a solid support, e.g., a multi-well plate or other assay device known to those of ordinary skill in the art. The capture antibody is allowed to attach for a period of time, e.g., overnight, and then unbound antibody is removed. The plate can then be washed to remove any unbound capture antibody. The plate can then be treated with a blocking solution to allow non-specific protein to bind to any unbound regions of the solid support. Typical blocking solutions include an unrelated protein, e.g., nonfat dry milk or serum albumin. The plate can then again be washed to remove any unbound blocking solution. Next, a sample suspected of containing DPP-4 is added to the plate. Samples are typically serially diluted and plated in duplicate or triplicate. Controls, including standard amounts of DPP-4 or a suitable fragment thereof and various negative controls are also included. The antigen is allowed to bind to the capture antibody for a period of time, e.g., one hour at room temperature. Following incubation, the plate can then be washed to remove any unbound antigen.

Next, a detection antibody is added. The detection antibody is typically an anti-DPP-4 antibody that binds to a different DPP-4 epitope than the capture antibody. The detection antibody can be labeled or unlabeled. Where the detection antibody is unlabeled, a labeled secondary antibody can be used for detection, as is well known by those of ordinary skill in the art. The detection antibody can be directly labeled with an enzyme, e.g., horseradish peroxidase or alkaline phosphatase, or can be labeled with a tag that will allow an enzyme to bind. For example the detection antibody can be conjugated to biotin, and the enzyme attached in a subsequent step by allowing enzyme-conjugated streptavidin to bind to the biotin tag. Alternatively the detection antibody can be conjugated to a chemiluminescent, fluorescent, or electrochemiluminescent tag. An example of the latter is a ruthenium chelate. Following incubation, the plate can then be washed to remove any unbound detection antibody.

Detection of the detection antibody is accomplished by methods that will vary based on the type of detection antibody that is used. If the detection antibody is tagged with biotin, then enzyme-conjugated streptavidin is added, unbound streptavidin is washed away, and a substrate is added which provides a colorimetric reaction that can be read, e.g., on a spectrophotometer. If the detection antibody is conjugated to a ruthenium chelate, the plate is subjected to electrical current, and light emission is measured.

In certain aspects, the method directly measures DPP-4 levels in a patient sample, where absolute levels are calculated by plotting the immunoassay results on a standard curve using, e.g., purified full length DPP-4 or a DPP-4 fragment. The detected signal from the detection antibody can then be quantitated based on the various standards and controls included on the plate. By plotting the results on a standard curve, the absolute levels or amount of DPP-4 in the test samples can be calculated, e.g., in ng/mL or pg DPP-4/mL protein.

In certain aspects of the immunoassay and method provided herein the capture antibody is mouse monoclonal antibody m3B7.6 as produced from a hybridoma deposited at the ATCC under Deposit No. PTA-121870 or an antigen-binding fragment, variant, or derivative thereof, or mouse monoclonal antibody m5B7.7 as produced from a hybridoma deposited at the ATCC under Deposit No. PTA-121871 or an antigen-binding fragment, variant, or derivative thereof. In certain aspects of the immunoassay and method provided herein the detection antibody is rat monoclonal antibody R11A2.15 as produced from a hybridoma deposited at the ATCC under Deposit No. PTA-121872 or an antigen-binding fragment, variant, or derivative thereof, or rat monoclonal antibody R11A9.11 as produced from a hybridoma deposited at the ATCC under Deposit No. PTA-121873 or an antigen-binding fragment, variant, or derivative thereof.

In certain aspects of the immunoassay and method provided herein the capture antibody is rat monoclonal antibody R11A2.15 as produced from a hybridoma deposited at the ATCC under Deposit No. PTA-121872 or an antigen-binding fragment, variant, or derivative thereof, or rat monoclonal antibody R11A9.11 as produced from a hybridoma deposited at the ATCC under Deposit No. PTA-121873 or an antigen-binding fragment, variant, or derivative thereof. In certain aspects of the immunoassay and method provided herein the detection antibody is mouse monoclonal antibody m3B7.6 as produced from a hybridoma deposited at the ATCC under Deposit No. PTA-121870 or an antigen-binding fragment, variant, or derivative thereof, or mouse monoclonal antibody m5B7.7 as produced from a hybridoma deposited at the ATCC under Deposit No. PTA-121871 or an antigen-binding fragment, variant, or derivative thereof.

In certain aspects of the immunoassay and method provided herein the capture antibody is mouse monoclonal antibody m3B7.6 as produced from a hybridoma deposited at the ATCC under Deposit No. PTA-121870 or an antigen-binding fragment, variant, or derivative thereof, and the detection antibody is rat monoclonal antibody R11A2.15 as produced from a hybridoma deposited at the ATCC under Deposit No. PTA-121872 or an antigen-binding fragment, variant, or derivative thereof. In certain aspects of the immunoassay and method provided herein the capture antibody is mouse monoclonal antibody m3B7.6 as produced from a hybridoma deposited at the ATCC under Deposit No. PTA-121870, or an antigen-binding fragment, variant, or derivative thereof, and the detection antibody is rat monoclonal antibody R11A9.11 as produced from a hybridoma deposited at the ATCC under Deposit No. PTA-121873 or an antigen-binding fragment, variant, or derivative thereof.

In certain aspects of the immunoassay and method provided herein the capture antibody is mouse monoclonal antibody m5B7.7 as produced from a hybridoma deposited at the ATCC under Deposit No. PTA-121871 or an antigen-binding fragment, variant, or derivative thereof, and the detection antibody is mouse monoclonal antibody R11A2.15 as produced from a hybridoma deposited at the ATCC under Deposit No. PTA-121872 or an antigen-binding fragment, variant, or derivative thereof. In certain aspects of the immunoassay and method provided herein the capture antibody is mouse monoclonal antibody m5B7.7 as produced from a hybridoma deposited at the ATCC under Deposit No. PTA-121871 or an antigen-binding fragment, variant, or derivative thereof, and the detection antibody is rat monoclonal antibody R11A9.11 as produced from a hybridoma deposited at the ATCC under Deposit No. PTA-121873 or an antigen-binding fragment, variant, or derivative thereof.

In certain aspects of the immunoassay and method provided herein the capture antibody is rat monoclonal antibody R11A2.15 as produced from a hybridoma deposited at the ATCC under Deposit No. PTA-121872 or an antigen-binding fragment, variant, or derivative thereof, and the detection antibody is mouse monoclonal antibody m3B7.6 as produced from a hybridoma deposited at the ATCC under Deposit No. PTA-121870 or an antigen-binding fragment, variant, or derivative thereof. In certain aspects of the immunoassay and method provided herein the capture antibody is rat monoclonal antibody R11A2.15 as produced from a hybridoma deposited at the ATCC under Deposit No. PTA-121872 or an antigen-binding fragment, variant, or derivative thereof, and the detection antibody is mouse monoclonal antibody m5B7.7 as produced from a hybridoma deposited at the ATCC under Deposit No. PTA-121871 or an antigen-binding fragment, variant, or derivative thereof.

In certain aspects of the immunoassay and method provided herein the capture antibody is rat monoclonal antibody R11A9.11 as produced from a hybridoma deposited at the ATCC under Deposit No. PTA-121873 or an antigen-binding fragment, variant, or derivative thereof, and the detection antibody is mouse monoclonal antibody m3B7.6 as produced from a hybridoma deposited at the ATCC under Deposit No. PTA-121870 or an antigen-binding fragment, variant, or derivative thereof. In certain aspects of the immunoassay and method provided herein the capture antibody is rat monoclonal antibody R11A9.11 as produced from a hybridoma deposited at the ATCC under Deposit No. PTA-121873 or an antigen-binding fragment, variant, or derivative thereof, and the detection antibody is mouse monoclonal antibody m5B7.7 as produced from a hybridoma deposited at the ATCC under Deposit No. PTA-121871 or an antigen-binding fragment, variant, or derivative thereof.

A variety of subject samples can be used in the methods presented herein. Exemplary, non-limiting examples of samples include one or more of whole blood, serum, plasma, saliva, sputum, nasal polyps, nasal mucus, bronchoalveolar lavage fluid, skin cells or lung tissue, e.g., lung epithelial cells. In specific aspects, the sample is a serum sample, skin cells or lung tissue.

In particular aspects, the methods disclosed herein include informing the subject of a result of the DPP-4 assay and/or of a diagnosis based at least in part on the DPP-4 level. The patient can be informed verbally, in writing, and/or electronically. This diagnosis can also be recorded in a patient medical record.

The term "medical record" or "patient medical record" refers to an account of a patient's examination and/or treatment that typically includes one or more of the following: the patient's medical history and complaints, the physician's physical findings, the results of diagnostic tests and procedures, and patient medications and therapeutic procedures. A medical record is typically made by one or more physicians and/or physicians' assistants and it is a written, transcribed or otherwise recorded record and/or history of various illnesses or injuries requiring medical care, and/or inoculations, and/or allergies, and/or treatments, and/or prognosis, and/or frequently health information about parents, siblings, and/or occupation. The record can, in some instances, be reviewed by a physician in diagnosing the condition.

The medical record can be in paper form and/or can be maintained in a computer readable medium. The medical record can be maintained by a laboratory, physician's office, a hospital, a healthcare maintenance organization, an insurance company, and/or a personal medical record website. In some aspects, a diagnosis, based at least in part on the DPP-4 level, is recorded on or in a medical alert article such as a card, a worn article, and/or a radiofrequency identification (RFID) tag. As used herein, the term "worn article" refers to any article that can be worn on a subject's body, including, but not limited to, a tag, bracelet, necklace, arm band, or head band.

In certain aspects, the methods can entail ordering and/or performing one or more additional assays. For example, if the DPP-4 level is determined to be within a normal range (i.e., not elevated), the DPP-4 assay can be repeated to rule out a false negative result, and/or one or more additional DPP-4 assays can be performed to monitor the subject's status. If the DPP-4 level is determined to be elevated, it can be desirable repeat the DPP-4 assay to rule out a false positive result.

DPP-4 Detection Methods, Assays, and Kits

This disclosure provides methods, assays, and kits to facilitate a determination or analysis of the DPP-4 level or amount of DPP-4 in the sample. In some aspects, the methods, assays, and kits disclosed herein are performed or used by a healthcare provider, a healthcare benefits provider, or a clinical laboratory to determine the DPP-4 level or amount of DPP-4 in the sample from the subject.

In certain aspects, the immunoassay is performed on a sample obtained from the patient, by the healthcare professional treating the patient, e.g., using an immunoassay as described herein, formulated as a "point of care" diagnostic kit. In some aspects, a sample is obtained from the patient and is submitted, e.g., to a clinical laboratory, for measurement of the DPP-4 level in the sample according to the healthcare professional's instructions, e.g., using an immunoassay as described herein.

In certain aspects, the patient having, or suspected of having, an IL-13-mediated disease or disorder has been diagnosed with a pulmonary disease or disorder, an inflammatory bowel disease or disorder, or a chronic inflammatory skin condition. In certain aspects, the disease or disorder having or suspected of having IL-13-mediated pathology is asthma, idiopathic pulmonary fibrosis (IPF), chronic obstructive pulmonary disease (COPD), ulcerative colitis (UC), atopic dermatitis, allergic rhinitis, or chronic rhinosinusitis.

This disclosure also provides kits for use in the practice of the immunoassays as disclosed herein. Such kits can comprise containers, each with one or more of the various reagents (e.g., in concentrated form) utilized in the methods, including, for example, one or more anti-DPP-4 antibodies. One or more anti-DPP-4 antibodies, e.g., capture antibodies can be provided already attached to a solid support, and one or more antibodies, e.g., detection antibodies, can be provided already conjugated to a detectable label, e.g., biotin or a ruthenium chelate. The kit can also provide reagents for coupling a detectable label to an antibody (as well as the label itself), buffers, and/or reagents and instrumentation to support the practice of the assays provided herein. In certain aspects, a labeled secondary antibody is provided that binds to the detection antibody. A kit provided according to this disclosure can further comprise suitable containers, plates and any other reagents or materials necessary to practice the assays provided herein.

A kit for measuring DPP-4 levels in a sample can comprise one or more of the anti-DPP-4 antibodies or fragments thereof provided herein, e.g., mouse monoclonal antibody m3B7.6 produced from a hybridoma deposited at the American Type Culture Collection (ATCC) under Deposit No. PTA-121870, mouse monoclonal antibody m5B7.7 produced from a hybridoma deposited at the ATCC under Deposit No. PTA-121871, rat monoclonal antibody R11A2.15 produced from a hybridoma deposited at the ATCC under Deposit No. PTA-121872, and/or rat monoclonal antibody R11A9.11 produced from a hybridoma deposited at the ATCC under Deposit No. PTA-121873, and/or antigen-binding fragments, variants or derivatives thereof, or related antibodies or antigen-binding fragments thereof, also as described herein.

In certain aspects, a kit as provided herein comprises two isolated antibodies or antigen-binding fragments thereof, a capture antibody and a detection antibody. In certain aspects the capture antibody is mouse monoclonal antibody m3B7.6 as produced from a hybridoma deposited at the ATCC under Deposit No. PTA-121870 or an antigen-binding fragment, variant, or derivative thereof, or mouse monoclonal antibody m5B7.7 as produced from a hybridoma deposited at the ATCC under Deposit No. PTA-121871 or an antigen-binding fragment, variant, or derivative thereof, and the detection antibody is rat monoclonal antibody R11A2.15 as produced from a hybridoma deposited at the ATCC under Deposit No. PTA-121872 or an antigen-binding fragment, variant, or derivative thereof, or rat monoclonal antibody R11A9.11 as produced from a hybridoma deposited at the ATCC under Deposit No. PTA-121873 or an antigen-binding fragment, variant, or derivative thereof.

In certain aspects the capture antibody is rat monoclonal antibody R11A2.15 as produced from a hybridoma deposited at the ATCC under Deposit No. PTA-121872 or an antigen-binding fragment, variant, or derivative thereof, or rat monoclonal antibody R11A9.11 as produced from a hybridoma deposited at the ATCC under Deposit No. PTA-121873 or an antigen-binding fragment, variant, or derivative thereof, and the detection antibody is mouse monoclonal antibody m3B7.6 as produced from a hybridoma deposited at the ATCC under Deposit No. PTA-121870, or an antigen-binding fragment, variant, or derivative thereof, or mouse monoclonal antibody m5B7.7 as produced from a hybridoma deposited at the ATCC under Deposit No. PTA-121871 or an antigen-binding fragment, variant, or derivative thereof.

In certain aspects of the kits provided herein, the capture antibody is mouse monoclonal antibody m3B7.6 as produced from a hybridoma deposited at the ATCC under Deposit No. PTA-121870, or an antigen-binding fragment, variant, or derivative thereof, and the detection antibody is rat monoclonal antibody R11A2.15 as produced from a hybridoma deposited at the ATCC under Deposit No. PTA-121872 or an antigen-binding fragment, variant, or derivative thereof. In certain aspects of the kits provided herein, the capture antibody is mouse monoclonal antibody m3B7.6 as produced from a hybridoma deposited at the ATCC under Deposit No. PTA-121870 or an antigen-binding fragment, variant, or derivative thereof, and the detection antibody is rat monoclonal antibody R11A9.11 as produced from a hybridoma deposited at the ATCC under Deposit No. PTA-121873 or an antigen-binding fragment, variant, or derivative thereof.

In certain aspects of the kits provided herein, the capture antibody is mouse monoclonal antibody m5B7.7 as produced from a hybridoma deposited at the ATCC under Deposit No. PTA-121871 or an antigen-binding fragment, variant, or derivative thereof, and the detection antibody is mouse monoclonal antibody R11A2.15 as produced from a hybridoma deposited at the ATCC under Deposit No. PTA-121872 or an antigen-binding fragment, variant, or derivative thereof. In certain aspects of the kits provided herein, the capture antibody is mouse monoclonal antibody m5B7.7 as produced from a hybridoma deposited at the ATCC under Deposit No. PTA-121871 or an antigen-binding fragment, variant, or derivative thereof, and the detection antibody is rat monoclonal antibody R11A9.11 as produced from a hybridoma deposited at the ATCC under Deposit No. PTA-121873 or an antigen-binding fragment, variant, or derivative thereof.

In certain aspects of the kits provided herein, the capture antibody is rat monoclonal antibody R11A2.15 as produced from a hybridoma deposited at the ATCC under Deposit No. PTA-121872 or an antigen-binding fragment, variant, or derivative thereof, and the detection antibody is mouse monoclonal antibody m3B7.6 as produced from a hybridoma deposited at the ATCC under Deposit No. PTA-121870 or an antigen-binding fragment, variant, or derivative thereof. In certain aspects of the kits provided herein, the capture antibody is rat monoclonal antibody R11A2.15 as produced from a hybridoma deposited at the ATCC under Deposit No. PTA-121872 or an antigen-binding fragment, variant, or derivative thereof, and the detection antibody is mouse monoclonal antibody m5B7.7 as produced from a hybridoma deposited at the ATCC under Deposit No. PTA-121871 or an antigen-binding fragment, variant, or derivative thereof.

In certain aspects of the kits provided herein, the capture antibody is rat monoclonal antibody R11A9.11 as produced from a hybridoma deposited at the ATCC under Deposit No. PTA-121873 or an antigen-binding fragment, variant, or derivative thereof, and the detection antibody is mouse monoclonal antibody m3B7.6 as produced from a hybridoma deposited at the ATCC under Deposit No. PTA-121870 or an antigen-binding fragment, variant, or derivative thereof. In certain aspects of the kits provided herein, the capture antibody is rat monoclonal antibody R11A9.11 as produced from a hybridoma deposited at the ATCC under Deposit No. PTA-121873 or an antigen-binding fragment, variant, or derivative thereof, and the detection antibody is mouse monoclonal antibody m5B7.7 as produced from a hybridoma deposited at the ATCC under Deposit No. PTA-121871 or an antigen-binding fragment, variant, or derivative thereof.

In certain aspects, the detection antibody is detectably labeled. In certain aspects, the detectable label is biotin and the detection reagents comprise a streptavidin-horse radish peroxidase (HRP) conjugate and a colorimetric substrate for HRP. In certain aspects the detectable label is a ruthenium chelate. Other antibodies, labels, and reagents as described elsewhere herein can also be used in kit as provided herein.

In certain aspects, this disclosure provides an immunoassay for detecting DPP-4 levels in one or more samples, comprising the use of at least one, e.g., at least two anti-DPP-4 antibodies or antigen-binding fragments, variants, or derivatives thereof, e.g., mouse monoclonal antibody m3B7.6 produced from a hybridoma deposited at the American Type Culture Collection (ATCC) under Deposit No. PTA-121870, mouse monoclonal antibody m5B7.7 produced from a hybridoma deposited at the ATCC under Deposit No. PTA-121871, rat monoclonal antibody R11A2.15 produced from a hybridoma deposited at the ATCC under Deposit No. PTA-121872, and/or rat monoclonal antibody R11A9.11 produced from a hybridoma deposited at the ATCC under Deposit No. PTA-121873 as described herein, or antigen-binding fragments, variants or derivatives thereof, or related antibodies or antigen-binding fragments thereof, also as described herein.

In certain aspects, the immunoassay provided herein is a sandwich immunoassay, e.g., an ELISA assay or an ECL assay, comprising a first anti-DPP-4 "capture" antibody or antigen-binding fragment thereof attached to a solid support, and a second anti-DPP-4 "detection" antibody or antigen-binding fragment thereof. The immunoassay is performed by methods provided herein or methods well known and understood by those of ordinary skill in the art. In one aspect the immunoassay comprises attaching a capture antibody, or fragment, variant, or derivative thereof to a solid support; applying the test sample or a control sample, allowing DPP-4, if present in the sample, to bind to the capture antibody, or fragment, variant, or derivative thereof; applying the detection antibody, or fragment, variant, or derivative thereof, which can bind to DPP-4 already bound to the capture antibody, or fragment, variant, or derivative thereof; and measuring the amount of detection antibody, or fragment, variant, or derivative thereof bound to DPP-4. In certain aspects, the assay can further include washing steps, blocking steps and incubation steps.

In certain aspects, the detection antibody, or fragment, variant, or derivative thereof further comprises a detectable label, e.g., biotin or ruthenium chelate.

Aspects of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

EXAMPLES

Example 1: Generation and Characterization of Rat and Mouse Monoclonal Antibodies Specific for Human DPP-4

Mouse and rat monoclonal antibodies specific for human DPP-4 were produced by the following method. Animals were immunized using the Repetitive Immunization at Multiple Sites (RIMMS) protocol (Kilpatrick, K., et al., Hybridoma 16:381-389 (2009)). Briefly, five Balb/c mice and two Wistar rats, all at ages 4-6 weeks, were injected at 6 dorsal sites subcutaneously with r-human DPP4-His (R&D Systems Catalog No. 1180) mixed in Complete Freund's adjuvant (Sigma) (for 1st round followed by incomplete Freund's adjuvant for subsequent immunizations) and 6 ventral sites subcutaneously with antigen mixed in TiterMax (Sigma) adjuvant on each dosing date. In total, each animal received injections at twelve sites as shown in FIG. 1. Test bleeds were collected on day 13, and both pre-bleed and immunized sera were tested by direct binding ELISA using DPP-4 (r-DPP-4-His, R&D Systems catalog number 1180) and negative control glycoprotein 130 (r-gp130-His) bound to the ELISA plates. Wells of high binding ELISA plates were coated with 50 μL of a 2 μg/mL solution of r-human DPP-4-His or gp130-His in PBS overnight at 4° C. The plates were then washed three times with 200 μL/well wash buffer (PBS/0.1% TWEEN-20®). Following washing, 150 µL/well blocking buffer (PBS/3% nonfat dry milk/0.1% TWEEN-20®) was added to each well, and the plates were incubated for one hour at room temperature. The plates were then washed three times as noted above.

Pre- and test-sera were serially diluted in PBS, pH7.2 buffer, from an initial 1:100 dilution to a final dilution of 1:218,600. Fifty µL of each diluted sample was added to the plates and incubated for 1 hour at room temperature. The plates were washed three times as noted above. Following washing, 50 µl of the detection antibody was added to each well. For the mouse group, Donkey anti-mouse (H+L):HRP (Jackson Immunoresearch, Catalog No. 715-035-151) diluted 1:8000 in PBS was used. For the rat group, Donkey anti-rat(H+L):HRP (Jackson Immunoresearch, Catalog No. 715-035-153), 1:8000 in PBS was used. The plates were incubated for 1 hour at room temperature. The plates were then washed three times and 50 µL/well TMB substrate (KPL, Catalog No. 52-00-04) pre-warmed to room temperature was added. The plates were incubated at room temperature in the dark for 10 minutes, and 50 µL of stop solution (1M HCl) was added to each well. The plates were read on a spectrophotometer at λ=450 nm.

Pre-bleed and immunized serum antibody titers for DPP-4 are shown in FIG. 2. On day 16 and 19, lymph nodes were collected from the rats and mice showing robust serum titer, and hybridomas were generated as follows. On day 19 lymph nodes were collected from the animals, lymphocyte cells were extracted from the lymphoid tissues and filtered through 70 µm cell strainers. Antigen specific B cells were isolated by using MACS, streptavidin microbeads (Miltenyi Biotec Catalog #130-048-101) using the manufacturer suggested protocol. The DPP4 specific B cells were then fused with myeloma P3x/63Ag8.653 cells at 1:1 ratio following the PEG (Roche) fusion method. Fused cells were seeded at a density of $2.5 \times 10^4$ B cell/well in hybridoma growth media (Ex-Cell 610+10% Hi-FBS+1% penicillin-streptomycin+1× BM-condimed H1 hybridoma cloning supplement) supplemented with 1×HAT. Seven days after fusion, HAT containing medium was replaced with growth medium supplemented with 1×HT.

Hybridoma supernatants were screened for antibodies binding to human DPP-4, and four hybridoma-produced antibodies were selected for further investigation: mouse monoclonal antibody m3B7.6 (IgG1/κ), mouse monoclonal antibody m5B7.7 (IgG1/κ), rat monoclonal antibody R11A2.15 (IgG2a/κ), and rat monoclonal antibody R11A9.11 (IgG2a/κ). Hybridoma cell lines expressing these four monoclonal antibodies were deposited under the Budapest Treaty at the American Type Culture Collection (ATCC) under Deposit No. PTA-121870 (m3B7.6), Deposit No. PTA-121871 (m5B7.7), Deposit No. PTA-121872 (R11A2.15), and Deposit No. PTA-121873 (R11A9.11) on Jan. 8, 2015.

Example 2: Sandwich ELISA Assays to Detect DPP-4

Materials and Methods
A. DPP-4 Sandwich ELISA Protocol with HRP Detection System.

HRP-based sandwich ELISA assays were performed as follows. Specific details such as anti-DPP-4 capture antibodies, samples to be tested, and anti-DPP-4 detection antibodies are noted for specific experiments in the various examples. Variations to standard ELISA protocols are well known to those of ordinary skill in the art, and can be used according to this disclosure.

High binding ELISA plates were coated with an anti-DPP-4 capture mAb, e.g., m3B7.6 or m5B7.7 (5 µg/mL in PBS; 50 µL/well), and were incubated overnight at 4° C. The plates were washed three times with 200 µL/well wash buffer (PBS/0.1% TWEEN-20®). Following washing, 150 µL/well block buffer (PBS/3% nonfat dry milk/0.1% TWEEN-20®) was added to each well, and the plates were incubated for one hour at room temperature. The plates were then washed three times as noted above.

For the standard curve, DPP-4 standards (e.g., standards available from R & D Systems Catalog #1180-SE) were serially diluted in PBS, pH7.2 buffer or 1% normal human serum, e.g., 2-fold dilutions from 500 ng/mL to 0.49 ng/ml. Fifty microliters (50 µL) of each standard or diluted sample was added to the plates, and the plates were incubated for 1 hour at room temperature. Again, the plates were washed three times as noted above. Following washing, 50 µL of detection mAb R11A2.15, R11A9.11 or 222113.11 (at 2 µg/ml) was added to each well, and the plates were incubated for 1 hour at room temperature. Again, the plates were washed three times as noted above. Following washing, 50 µL of Donkey anti-Rat(H+L)-HRP conjugate (Jackson Immunoresearch catalog #712-035-153), diluted 1:8,000 in PBS was added to each well, and the plates were incubated for one hour at room temperature. Again, the plates were washed three times as noted above. Following washing, 50 µL/well TMB substrate (KPL, Catalog No. 52-00-04), pre-warmed to room temperature was added, the plates were incubated at room temperature in the dark for 10 minutes, and 50 µL of TMB stop solution (1M HCl) was added to each well. Finally the plates were read on a spectrophotometer at λ=450 nm.

Results

The results using mouse m3B7.6 and m5B7.7 as the capture antibodies are shown in FIG. 3A and FIG. 3B, respectively. The two mouse and two rat mAbs (mAb R11A2.15 or R11A9.11) form four different pairs of detecting agents for human CD26 with similar lower limits of detection (LLOD) and provided high sensitivity in measuring human DPP-4 in a sandwich ELISA assay. In contrast, the commercially available rat mAb (R222113) (Human DPPIV/CD26 MAb (Clone 222113), Rat IgG2A Catalog No. MAB1180 from R&D Systems) detected less human CD26 and was significantly less sensitive in measuring human DPP-4 in a sandwich ELISA assay when paired with the two mouse mAbs m3B7.6 and m5B7.7. See FIGS. 3A-B. These results demonstrate that the antibodies provided herein (m3B7.6, m5B7.7, R11A2.15 and R11A9.11) are superior in detecting human CD26 in an immunoassay compared to the commercially available rat antibody R222113. In addition, the antibodies provided herein (m3B7.6, m5B7.7, R11A2.15 and R11A9.11) detect both endogenous and recombinant human CD26 making them useful as diagnostic reagents.

As shown in FIG. 3, m3B7.6+R11A2.15, m3B7.6+R11A9.11, m5B7.7+R11A2.15 and/or m5B7.7+R11A9.11 are effective in measuring human DPP-4 in a sandwich ELISA assay. In addition, regardless of the choice of pairs, the serum concentration of DPP-4 in the study was between to 1-2 µg/ml.

Example 3: Anti-DPP-4 mAb Epitope Binning Using OCTET

Epitope binning for the four anti-DPP-4 antibodies (m3B7.6, m5B7.7, R11A2.15 and R11A9.11) was carried out by OCTET. Test antibody was biotinylated and captured on a streptavidin biosensor at concentration of 20 µg/ml and in 200 Owen for 5 min and then washed with 200 µL of PBS buffer for 1 min. The biosensor was then incubated with recombinant human DPP4 at 10 µg/mL for 5 min and was washed with 200 µL of PBS buffer for 1 min. The competitor antibodies were mixed in at a 1:1 ratio with the testing at a final concentration of 20 µg/ml and incubated with the biosensor in 200 µl for 5 min.

A schematic of the assay is shown in

Figure 4A:
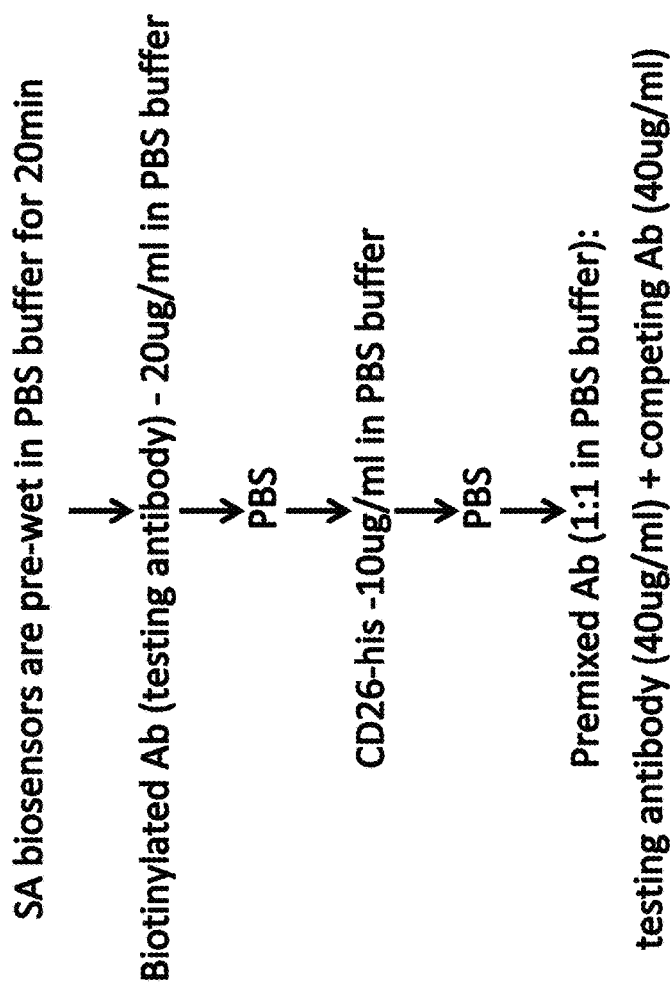
Figure 4B:
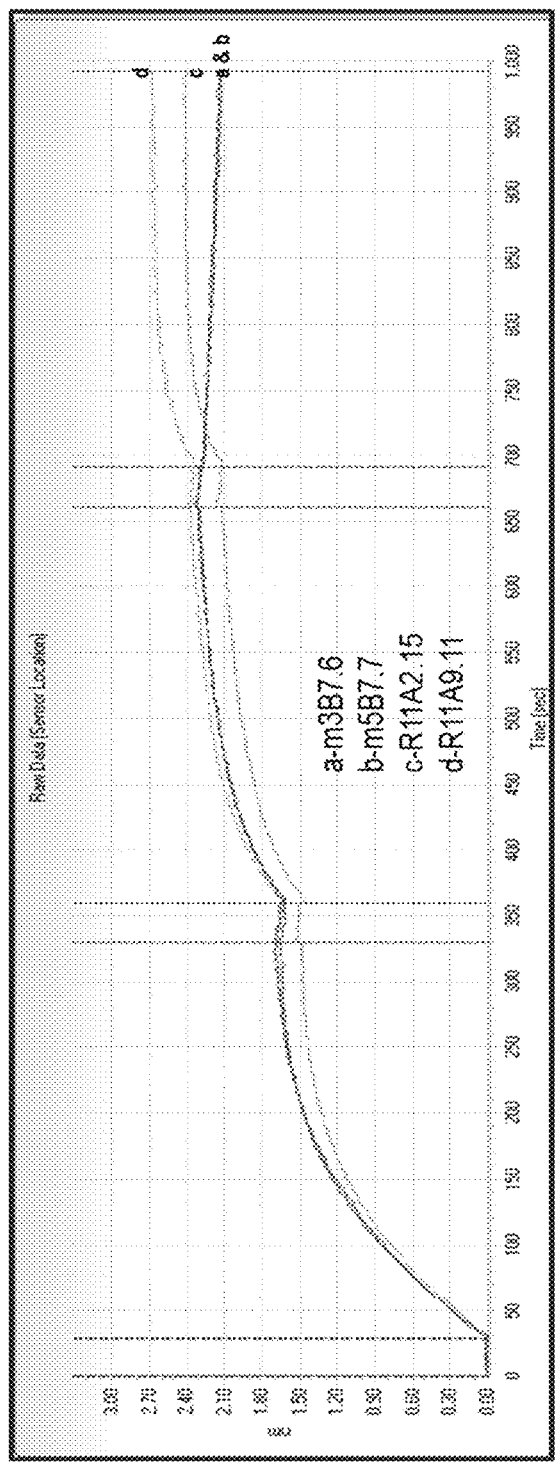
Figure 4C:
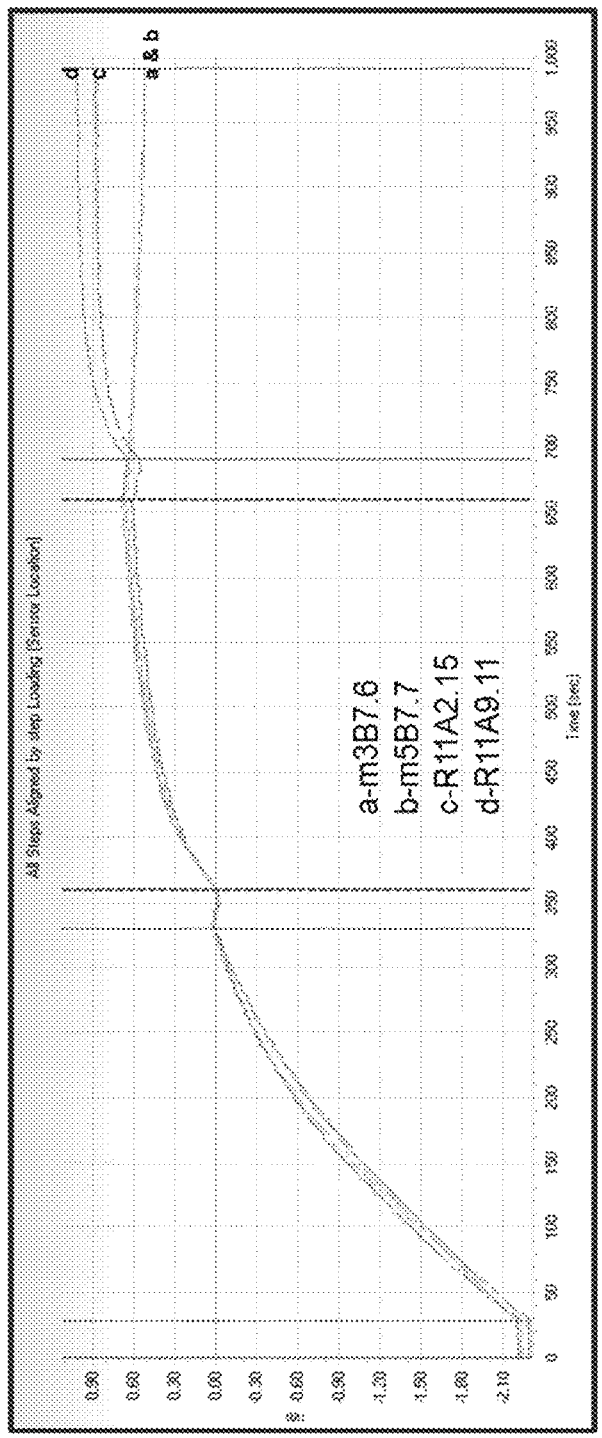
Figure 4D:
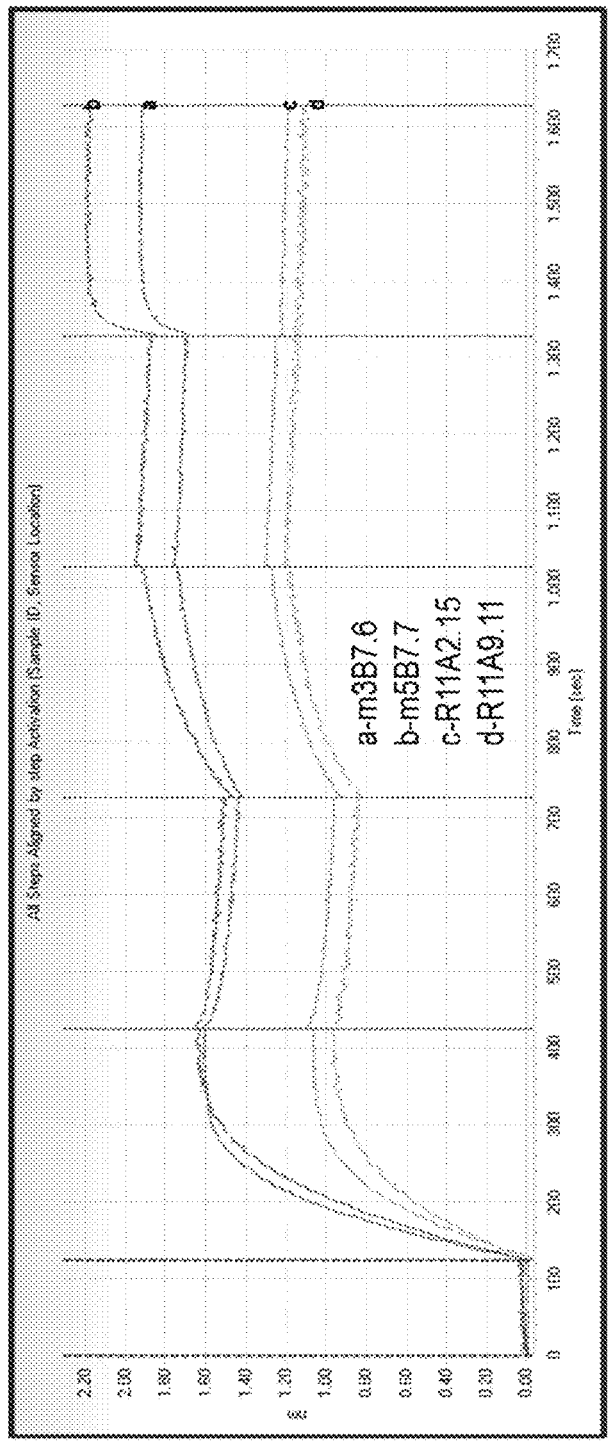
Figure 4E:
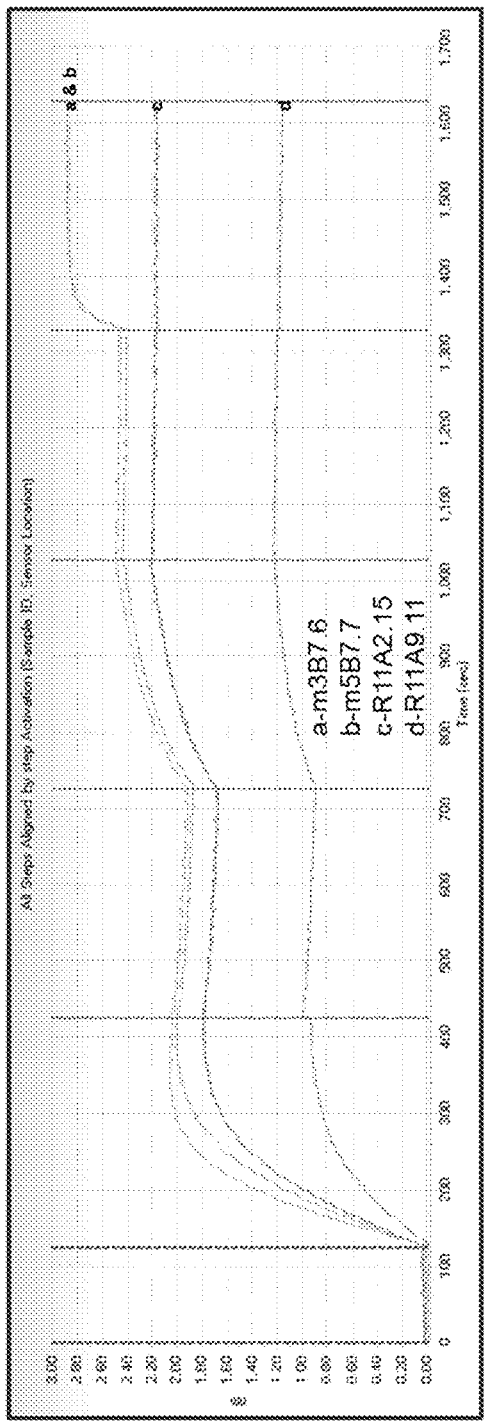

FIG. 4A, and the results with the four different antibodies (m3B7.6, m5B7.7, R11A2.15 and R11A9.11) as the testing antibody are shown in FIGS. 4B-E, respectively. The results demonstrated that the mouse monoclonal antibodies m3B7.6 and m5B7.7 compete with each other, and that the rat monoclonal antibodies R11A2.15 and R11A9.11 compete with each other. The mouse antibodies do not compete with the rat antibodies, and thus do not share an epitope. Based on this data, we conclude that the two mouse antibodies (m3B7.6 and m5B7.7) share the same or an overlapping epitope while the two rat antibodies (R11A2.15 and R11A9.11) share an epitope or an overlapping epitope that is different from the epitope shared by the mouse antibodies.

The foregoing description of the specific aspects will so fully reveal the general nature of the disclosure that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. An isolated antibody that binds to human dipeptidyl peptidase-4 (DPP-4), comprising a heavy chain variable domain (VH) with three heavy chain complementarity determining regions (CDRs) VHCDR1, VHCDR2 and VHCDR3, and a light chain variable domain (VL) with three light chain CDRs VLCDR1, VLCDR2, and VLCDR3, wherein the six CDRs of the isolated antibody are identical to the six CDRs of mouse monoclonal antibody m3B7.6 produced from a hybridoma deposited at the American Type Culture Collection (ATCC) under Deposit No. PTA-121870, mouse monoclonal antibody m5B7.7 produced from a hybridoma deposited at the ATCC under Deposit No. PTA-121871, rat monoclonal antibody R11A2.15 produced from a hybridoma deposited at the ATCC under Deposit No. PTA-121872, or rat monoclonal antibody R11A9.11 produced from a hybridoma deposited at the ATCC under Deposit No. PTA-121873.

2. The isolated antibody of claim 1, comprising a VH and a VL identical to the VH and VL of mouse monoclonal antibody m3B7.6 produced from a hybridoma deposited at the American Type Culture Collection (ATCC) under Deposit No. PTA-121870, mouse monoclonal antibody m5B7.7 produced from a hybridoma deposited at the ATCC under Deposit No. PTA-121871, rat monoclonal antibody R11A2.15 produced from a hybridoma deposited at the ATCC under Deposit No. PTA-121872, or rat monoclonal antibody R11A9.11 produced from a hybridoma deposited at the ATCC under Deposit No. PTA-121873.

3. The antibody of claim 1, which further comprises a heterologous polypeptide fused thereto.

4. The antibody of claim 3, wherein the heterologous polypeptide is a stabilizing polypeptide, a tag, a label, or a combination thereof.

5. The antibody of claim 1, which is conjugated to a heterologous moiety.

6. The antibody of claim 5, wherein the heterologous moiety comprises one or more of: a peptide, a protein, an enzyme, a lipid, a heterologous antibody or fragment thereof, a detectable label, or polyethylene glycol (PEG).

7. The antibody of claim 6, wherein the heterologous moiety comprises biotin or a ruthenium chelate.

8. A composition comprising the antibody of claim 1.

9. A composition comprising a combination of at least two antibodies, wherein each of the at least two antibodies comprises six CDRs of mouse monoclonal antibody m3B7.6 produced from a hybridoma deposited at the American Type Culture Collection (ATCC) under Deposit No. PTA-121870, mouse monoclonal antibody m5B7.7 produced from a hybridoma deposited at the ATCC under Deposit No. PTA-121871, rat monoclonal antibody R11A2.15 produced from a hybridoma deposited at the ATCC under Deposit No. PTA-121872, or rat monoclonal antibody R11A9.11 produced from a hybridoma deposited at the ATCC under Deposit No. PTA-121873.

10. A hybridoma selected from the group consisting of the hybridoma deposited at the American Type Culture Collection (ATCC) under Deposit No. 121870, the hybridoma deposited at the ATCC under Deposit No. 121871, the hybridoma deposited at the ATCC under Deposit No. 121872, the hybridoma deposited at the ATCC under Deposit No. 121873.

11. An isolated antibody produced by the hybridoma of claim 10.

12. A composition comprising an antibody produced by the hybridoma of claim 10.

13. An antibody-producing cell culture comprising: a hybridoma deposited at the American Type Culture Collection (ATCC) under Deposit No. 121870, a hybridoma deposited at the ATCC under Deposit No. 121871, a hybridoma deposited at the ATCC under Deposit No. 121872, or a hybridoma deposited at the ATCC under Deposit No. 121873.

14. An isolated antibody produced by the antibody-producing cell culture of claim 13.

15. A composition comprising an antibody produced by the cell culture of claim 13.

* * * * *